United States Patent [19]

Wakabayashi et al.

[11] 4,249,934

[45] Feb. 10, 1981

[54] 1,2-ALKYLENE-4-SUBSTITUTED URAZOLE HERBICIDES

[75] Inventors: Osamu Wakabayashi, Kawasaki; Kuni Matsuya, Yokohama; Hiroki Ohta, Machida; Tetsuo Jikihara; Seiichi Suzuki, both of Yokohama, all of Japan

[73] Assignee: Mitsubishi Chemical Industries, Limited, Tokyo, Japan

[21] Appl. No.: 943,810

[22] Filed: Sep. 19, 1978

Related U.S. Application Data

[63] Continuation-in-part of Ser. No. 727,986, Sep. 29, 1976, abandoned, and a continuation-in-part of Ser. No. 681,454, Apr. 29, 1976, abandoned, said Ser. No. 727,986, and Ser. No. 681,454, is a continuation-in-part of Ser. No. 586,276, Jun. 12, 1975, abandoned.

[30] Foreign Application Priority Data

| Jun. 19, 1974 | [JP] | Japan | 49-70049 |
| Sep. 11, 1974 | [JP] | Japan | 49-104608 |
| Sep. 13, 1974 | [JP] | Japan | 49-105569 |
| Sep. 18, 1974 | [JP] | Japan | 49-107341 |
| Oct. 4, 1974 | [JP] | Japan | 49-114516 |
| Nov. 18, 1974 | [JP] | Japan | 49-132492 |
| Dec. 19, 1974 | [JP] | Japan | 49-146160 |
| Dec. 27, 1974 | [JP] | Japan | 49-603 |
| Jan. 20, 1975 | [JP] | Japan | 50-8544 |

[51] Int. Cl.$^3$ .................... A01N 43/64; C07D 487/04
[52] U.S. Cl. ........................ 71/92; 544/236; 548/264
[58] Field of Search .......... 71/92; 544/236; 260/308 C; 548/264

[56] References Cited

U.S. PATENT DOCUMENTS

| 3,704,743 | 12/1972 | Moon | 424/250 |
| 3,912,735 | 10/1975 | VonBredon | 260/308 |
| 3,925,379 | 12/1975 | VonBredon et al. | 424/200 |
| 4,049,820 | 9/1977 | Shigematsu et al. | 260/308 C |

OTHER PUBLICATIONS

Zinner et al., Chem. Abs. 59, 5152a (1963).

*Primary Examiner*—Mark L. Berch
*Attorney, Agent, or Firm*—Bierman & Bierman

[57] ABSTRACT

Disclosed is a novel 1,2-alkylene-4-substituted urazole derivative which has unique biological activities, especially a herbicidal or weeding activity.

29 Claims, No Drawings

1,2-ALKYLENE-4-SUBSTITUTED URAZOLE HERBICIDES

This is a continuation-in-part application of Ser. No. 681,454, filed Apr. 29, 1976, and Ser. No. 727,986, filed Sept. 29, 1976, both of which are continuation-in-part applications of Ser. No. 586,276, all abandoned filed June 12, 1975, and which claims the priority of Japanese Patent Application No. 70049/1974, filed June 19, 1974; No. 104608/1974, filed Sept. 11, 1974; No. 105569/1974, filed Sept. 13, 1974; No. 107341/1974, filed Sept. 18, 1974; No. 114,516/1974, filed Oct. 4, 1974; No. 132492/1974, filed Nov. 18, 1974; No. 146160/1974, filed Dec. 19, 1974; No. 603/1975, filed Dec. 27, 1974; No. 8544/1975, filed Jan. 20, 1975; and No. 226/1976, filed Jan. 1, 1976.

This invention relates to a novel urazole derivative and, in more particular, to a novel urazole derivative having a substituted phenyl on nuclear nitrogen in 4-position which have valuable biological activities.

It has already been known that certain 1,2-alkylene-4-substituted urazole compounds, such as 1,2-trimethylene-4-phenylurazole 1,2-tetramethylene-4-phenylurazole and 1,2-pentamethylene-4-phenylurazole are synthesized but their biological activities especially herbicidal activity have yet not been found [refer to G. Zinner and W. Deucker: Arch. Pharm. 296 13 (1963) and R. C. Cookson et al: J. Chem. Soc. 1967, 1905].

Accordingly, an object of this invention is to provide a novel urazole derivative having unique herbicidal activity.

Another object is to provide an improved commercially applicable process for producing such urazole derivatives.

Still another object is to provide a herbicidal composition comprising such urazole derivative as active ingredient.

Such urazole derivatives according to this invention are represented by general formula I:

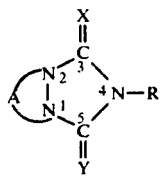

(I)

wherein A represents alkylene or alkenylene containing 1 to 8 carbon atoms which may be substitued by at least one methyl group, X and Y represent oxygen or sulfur, respectively, but when A is alkenylene both X and Y are sulfur, and R represents phenyl which may be substituted with at least one halogen, lower alkyl, lower alkoxy, nitro, halogenated benzyloxy and trihalomethyl; naphthyl; lower alkyl; lower alkenyl or cycloalkyl.

The compounds according to this invention can be prepared by various routes. Where both X and Y in general formula I are oxygen, then the compound is prepared by either route A or B.

On the other hand, where, in general formula I, X is oxygen or sulfur and Y is sulfur, the compound is prepared by route C or D and where X and Y are sulfur by route E.

Route A

The compounds of 1,2-alkylene-4-substituted urazoles according to this invention are prepared by reacting a salt of 4-substituted urazole represented by general formula III with an alkylene dihalide represented by formula IV:

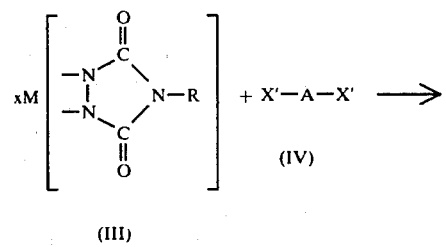

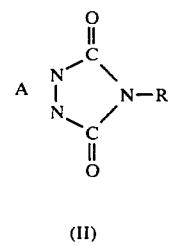

(II)

wherein R and A have the same meanings as above, X' represents halogen, M represents a metal or amine of monovalent or bivalent and x is 2 when M is monovalent or 1 when M is bivalent.

4-Substituted urazole which is a starting material of this process may be prepared by various procedures from hydrazine hydrate; from a commercial point of view, such substituted urazole is conveniently prepared by, for example, reacting hydrazine with chlorocarbonic ester or isocyanic acid to obtain 1-carboalkoxy hydrazine or carbamoyl hydrazine followed by reacting with isocyanate represented by RNCO (wherein R has the same meaning as above) to produce corresponding 4-substituted- 1-carboalkoxy semicarbazide (RHNCO—NH—NH—COOR) or 1-substituted biurea (RHN.CO—NH—NH—CONH$_2$) and cyclizing it by using an alkali, such as sodium hydroxide, potassium hydroxide, ammonium hydroxide, sodium alcoholate and potassium alcoholate. The resulting 4-substituted urazole derivative may be purified, if desired, by mean of recrystallization from an appropriate solvent such as ethanol.

One embodiment of the production of 4-(4'-bromophenyl)urazole which is the starting material will be explained by way of the following Reference Example.

REFERENCE EXAMPLE

A mixture of 0.1 mole of 4-(4'-bromophenyl)-1-carbethoxycarbamoyl hydrazine and 50 ml of 4 N aqueous potassium hydroxide was heated on a water bath for one hour to effect the reaction and the reaction mixture was subjected to filtration. The filtrate was allowed to cool to room temperature and was brought to acid by addition of 17 ml of concentrated hydrochloric acid. Then the solid material precipitated was separated by filtration, washed with water and dried to obtain a solid product weighing 23.0 g (yield being 90%).

The elementary analysis as C$_8$H$_6$O$_2$N$_3$Br was:

| | C% | H% | N% | Br% |
|---|---|---|---|---|
| Calculation | 37.52 | 2.36 | 16.41 | 31.21 |
| Found | 37.82 | 2.41 | 16.27 | 30.98 |

It was identified as 4-(4'-bromophenyl)urazole.

In carrying out the procedures of Route A, 4-substituted urazole derivative is reacted with 2 to 2.5 times molar a salt-forming base which includes, for example, hydroxides of sodium, potassium, ammonium, calcium, magnesium and barium; carbonates of sodium and potassium; alcoholates of sodium and potassium; amides of sodium and potassium; ammonia, a trialkyl amine, pyridine, picoline and sodium hydride, to form a salt of 4-substituted urazole.

The salt-forming reaction is conveniently effected in the presence of an appropriate solvent including water, a lower alcohol, dimethylformamide, tetrahydrofuran, liquid ammonia and benzene at a temperature of −40° to 100° C. with agitation. The reaction mixture containing urazole salt thus formed is subjected to cycloalkylation either without or with dilution by 5 to 50 times by weight of an appropriate solvent other than employed in such salt-forming reaction.

The cycloalkylation is performed by using a cycloalkylating agent represented by X′—A—X′ above in an amount of, generally, 1 to 1.2 times molar such urazole salt at a temperature of from room temperature to 200° C. for a half to five hours with agitation.

Examples of the cycloalkylating agent which may be employed according to this invention include, for example, an alkylhalide, such as 1,2-dichloroethane, 1,2-dibromoethane, 1,2diiodoethane, 1,3-dichloropropane, 1,3-dibromopropane, 1,3-diiodopropane, 1-bromo-3-iodopropane, 1,3-dibromobutane, 1,3-diiodobutane, 1,4-dichlorobutane, 1,4-dibromobutane, 1,4-diiodobutane, 1-chloro-4-bromobutane, 1,4-dibromo-2-methylbutane, 1,4-dibromopentane, 1,4-diidopentane, 2,4-dibromopentane, 1,5-dibromopentane, 1,5-diiodopentane, 1,4-dibromo-3-methylpentane, 1,5-dibromo-3-methylpentane, 2,5-dibromohexane, 2,5-diiodohexane, 1,5-dibromohexane, 1,6-dibromohexane, 1,6-diiodohexane, 1,6-dibromo-3-methylhexane, 1,7-dibromoheptane, 1,8-dibromooctane and 1,8-diiodooctane, and bromides and iodides are convenient because they are easy to handle and give high yield. Examples of solvent which may be used in the cycloalkylation reaction include, for example, water, an alcohol such as methanol, ethanol, n-propanol, iso-butanol and cyclohexanol, an aromatic hydrocarbon such as benzene, toluene and cumene, an ether such as dioxane, dipropyl ether and di-iso-butyl ether, a ketone, such as acetone, methyl ethyl ketone and cyclohexanone, an aprotic polar solvent such as N,N-dimethylformamide, dimethyl acetamide, N-methyl pyrolidone, dimethyl sulfoxide, sulforane, hexamethylphosphoric triamide, N-methylpyridine and N,N-diethylaniline alone or a mixture thereof.

The reaction product can be isolated by either adding to the reaction mixture water, petroleum ether or benzene to precipitate the product or concentrating the reaction mixture and washing the residue with water. If desired, the product is subjected to a conventional purification, for example, recrystallization from an appropriate solvent such as ethanol, chromatography or combination thereof.

ROUTE B

This route involves catalytic hydrogenation of a 1,2-(2'-butenylene)-4-substituted urazole derivative in a solvent in the presence of a reduction catalyst to prepare a 1,2-alkylene-4-substituted urazole derivative:

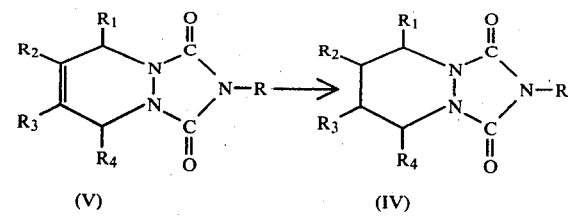

(V)　　　　　　　(IV)

wherein $R_1$, $R_2$, $R_3$ and $R_4$ represent hydrogen or methyl, respectively, and R has the same meaning as above.

Examples of the reduction catalyst which may be employed in this process include, for example, platinum oxide, a noble metal catalyst such as platinum, palladium, rhodium and ruthenium and a metal catalyst, such as Raney nickel and Raney cobalt, and palladium, platinum and platinum oxide catalysts are preferable.

The conditions under which the reaction is carried out such as temperature and pressure may vary depending upon type of the catalyst employed, and in general the reaction temperature ranges from 0° to 100° C., preferably 10° to 30° C. and the reaction pressure ranges from 1 to 100 kg/cm², preferably 1 to 15 kg/cm².

The solvent which may be employed in the process may be any solvent so far as it is used for a conventional catalytic hydrogenation of double bond, including, for example, water, a lower alcohol, such as methanol and ethanol, a lower aliphatic acid, such as acetic acid, a lower aliphatic ester, such as ethyl acetate, and dioxane, and methanol and ethyl acetate are preferable.

The starting material of Route B, 1,2-(2'-butenylene)-4-substituted urazole derivative is prepared by Diels-Alder reaction of a diene compound and a 4-substituted dehydrourazole:

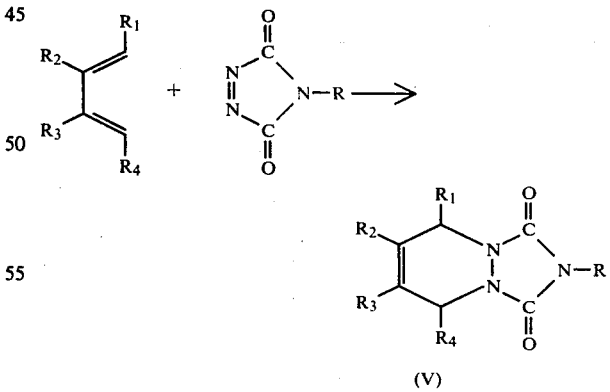

(V)

wherein $R_1$, $R_2$, $R_3$, $R_4$ and R have the same meanings as above.

This reaction is carried out by using 4-substituted dehydrourazole previously prepared through Diels-Alder reaction, but it is also possible to operate by adding to a mixture of such 4-substituted urazole and diene an oxidizing agent such as lead tetranitrate, lead tetraacetate, t-butyl hypochloride and nitrogen peroxide.

The resulting 1,2-(2'-butenylene)-4-substituted urazole derivative may be isolated by known purification technique such as recrystallization from ethanol-benzene, chromatography and others.

ROUTE C

This route is intramolecular condensation or cyclization of 1,2-alkylene-1-carboalkoxy(carboalkylthio, thionocarboalkoxy or dithiocarboalkoxy)-2-(N-substituted thiocarbamoyl)hydrazine to form the object compound:

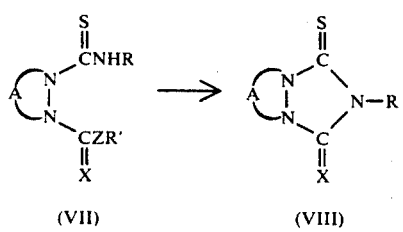

(VII)          (VIII)

wherein A, R and X have the same meanings as above, Z represents oxygen or sulfur and R' represents lower alkyl.

Among the starting materials of this process, 1,2-alkylene-1-carboalkoxy-2-(N-substituted thiocarbamoyl)hydrazine (that is, in formula VII, X and Z are oxygen) is prepared as follows.

For example, hydrazine hydrate is reacted with a carboalkoxylating agent, such as alkyl chloroformate and dialkyl carbonate to obtain a dialkylhydrazine dicarboxylate derivative (refer to Org. Synth. Coll. 3, 375) which is then cycloalkylated by an alkylene dihalide to obtain 1,2-alkylene-1,2-dicarboalkoxy hydrazine [refer to G. Zinner and W. Deucker: Arch. Pharm. 295, 526 (1962)]. The product is decarboxylated by KOH/alcohol to obtain 1,2-alkylene-1-carboalkoxy hydrazine which is reacted with isothiocyanate represented by RNCS (wherein R has the same meaning as above) to give the desired compound.

On the other hand, 1,2-alkylene-1-thionocarboalkoxy-2-(N-substituted thiocarbamoyl)hydrazine, that is X is sulfur and Z is oxygen is prepared by for example reacting 1,2-alkylene-hydrazine with a isothiocyanate represented by RNCS (wherein R has the same meaning as above) to give 1,2-alkylene-2-(N-substituted thiocarbamoyl)hydrazine which is reacted with alkyl chlorothio formate represented by ClCSOR' (wherein R' has the same meaning as above); alternatively 1,2-alkylene hydrazine is reacted subsequently with such formate and isothiocyanate.

The reaction mixture containing the product of formula VII thus formed may be subjected directly without isolation to intramolecular condensation.

The condensation is advantageously carried by heating a solution of compound VIII in an appropriate solvent under reflux, however, it is also possible to operate without using solvent at a temperature of 100° to 150° C.; examples of solvent which may be employed in this process include, for example, an aromatic hydrocarbon, such as benzene, toluene, xylene, cumene, chlorobenzene and nitrobenzene, a halogenated aliphatic hydrocarbon such as chloroform and carbon tetrachloride, petroleum having a boiling point ranging 50° to 200° C., an ether such as iso-propyl ether, an aprotic polar solvent, such as dimethylformamide, dimethyl sulfoxide and tetrahydrofuran and a lower alcohol, such as ethanol and iso-butanol. The amount of solvent to be used is not critical but in general, 10 to 50 times by weight compound VII is preferred. The condensation is conveniently facilitated by addition, in an amount of 0.001 to 1.0 time molar compound VII, of a catalyst including, for example, an alkoxide such as sodium ethoxide, sodium methoxide, potassium ethoxide and magnesium methoxide, an alkali metal hydroxide, such as potassium hydroxide and sodium hydroxide an alkali metal salt of aliphatic acid, such as sodium acetate and potassium acetate and a tertiary amine such as triethylamine and pyridine.

The reaction product may be isolated by either adding to the reaction mixture, for example, water, petroleum ether, n-hexane and benzene to precipitate the product, or distilling of the solvent from the reaction mixture and washing the residue with water. If desired, the product may be further purified by recrystallization from an appropriate solvent, such as ethanol, distillation, chromatography and any combination thereof.

ROUTE D

In this route, a 1,2-alkylene-N-substituted urazole is reacted with a sulfur-introducing agent to give a 1,2-alkylene-N-substituted thio(or dithio)urazole derivative:

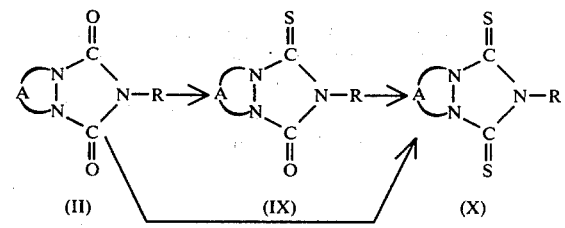

(II)          (IX)          (X)

wherein A and R have the same meanings as above.

The sulfur-introducing reaction according to this route is performed by heating a mixture of the urazole derivative, a solvent and a sulfur-introducing agent under reflux condition. The sulfur-introducing agent is preferably phosphorous pentasulfide. Examples of the solvent which may be employed in this route include, for example, preferable an aromatic hydrocarbon, such as benzene, toluene, xylene and cumene, and in some case where such urazole derivative dissolves slightly, also include pyridine, picolin and N,N-dimethylformamide. The amount of solvent to be used is in general 5 to 100 times by weight the urazole derivative.

Alternatively, the reaction is carried out at room temperature by reacting the urazole derivative with boron trisulfide or silicon disulfide in chloroform.

According to this route, monothio derivative or dithio derivative may be selectively produced by controlling the proportion of the starting material to the sulfur-introducing agent. That is, an equimolecular amount of the sulfur-introducing agent against carbonyl group in the starting material gives a dithio derivative and one-half equimolecular gives a monothio derivative.

Monothiourazole derivative which may be produced by either using one-half equimolecular of the sulfur-introducing agent or intramolecular condensation of 1,2-alkylene-1-carboalkoxy-2-(N-substituted thiocarbamoyl)hydrazine, may be converted into a dithio derivative by reacting with further sulfur-introducing agent.

From a commercial view-point, phosphorous pentasulfide is the preferred sulfur-introducing agent.

The amount of sulfur-introducing agent may vary depending upon kind of the object compound, and in general there is used 1 to 3 moles per one mole of the starting urazole derivative.

After completing the reaction, the reaction mixture is filtered, and the filtrate is concentrated to obtain the object compound.

For the further purification, the abovementioned technique may be applied.

ROUTE E

This route involves a reaction of a 1,2-alkylene-1-(N-substituted thiocarbamoyl)hydrazine and carbon disulfide:

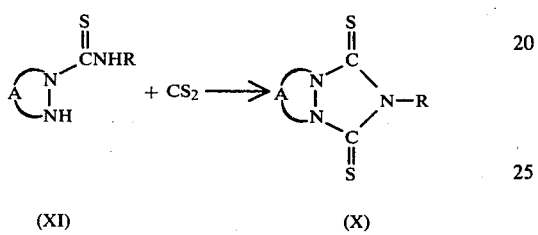

(XI)         (X)

wherein A and R have the same meanings as above.

The starting material (XI) of this process is usually obtained by either of two ways as follow:

(a) As shown in Route (C), reacting 1,2-alkylene-1-(N-substituted thiocarbamoyl)-2-carboalkoxy hydrazine with an alcoholic solution of alkali metal hydroxide such as $KOH/C_2H_5OH$ or (b) reacting hydrazine hydrate with a cyclic dicarboxylic anhydride, such as succinic anhydride, maleic anhydride, glutaric anhydride and adipic anhydride to obtain a cyclic hydrazide followed by reducing and reacting with an isothiocyanate:

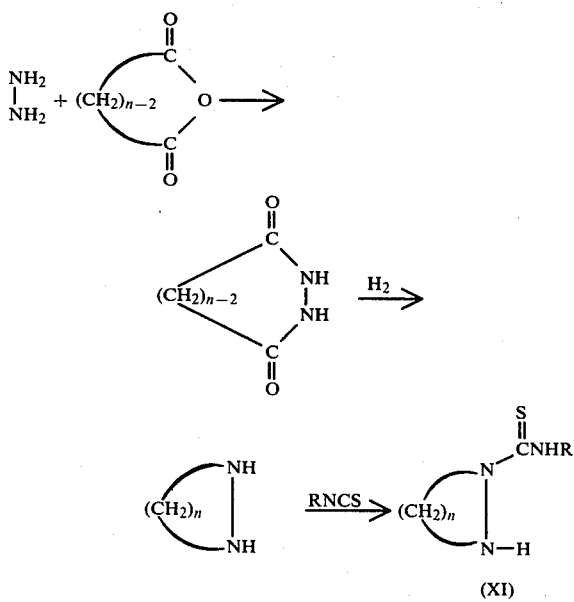

wherein R has the same meaning as above and $(CH_2)_n$ has the same meaning of A above.

In route E above, it is presumed that the reaction may proceed with through a transient product, which is not isolated, according to following scheme:

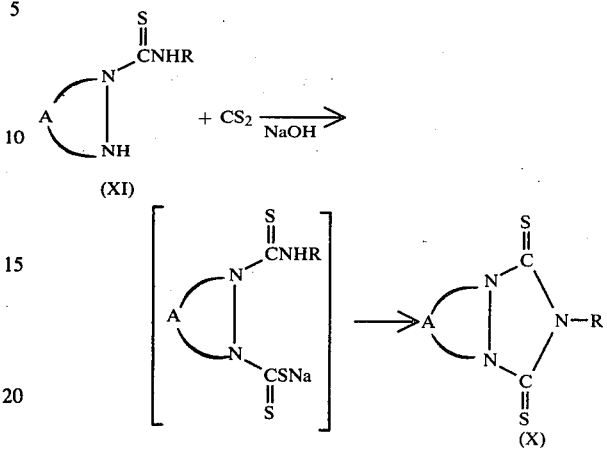

wherein A and R have the same meanings as above.

In route E above, a mixture of 1,2-alkylene-1-(N-substituted thiocarbamoyl)hydrazine, carbon disulfide in an amount of 1 to 10 times molar such hydrazine derivative, an alkali and an appropriate solvent is heated under reflux for 1 to 5 hours, said alkali being, for example, sodium hydroxide, potassium hydroxide and ammonium hydroxide and likes and the solvent being an alcohol, such as methanol and N,N-dimethylformamide.

The amount of said solvent and alkali material on the basis of said starting material is, respectively, 5 to 100 times by weight and 0.5 to 1.5 times molar.

Upon completing the reaction, the solvent and excess carbon disulfide are removed by distillation and the residue is brought to neutral by addition of a diluted acid to separate the desired product.

The herbicide according to this invention comprises as active ingredient an urazole derivative represented by formula I, which possesses unique applicability to soil treatment and foliage treatment, and excellent herbicidal activity against grasses such as *Digitaria adscendens, Eleusine indica, Echinochloa crusgalli, Poa annua, Cyperus esculentus* and *Alopecurus aequalis* and weeds such as *Siegesbeckia pubescens, Amaranthus lividus, Polygonum persicaris, Chenopodium album, Lamium amplexicaule, Acalypha australis, Galinsogo ciliate, Plantago asiatica, Portulaca oleracea, Commelina communis, Pinellia ternata* and *Artemisia princeps,* as well as improved control against perennial weeds such as *Eleocharis acicularis* and Room et Schult.

We have conducted intensive studies in order that properties in absorption, translocation etc. are given to this compound and the herbicidal activity is increased as well as crop injury or phytotoxicity and a tendency of environmental pollution are decreased; especially our efforts have been focused to find out a compound which is easily broken down by microorganisms in soil and non-persistence in plants, that is, readily biodegradable materials. As a result it has been found that novel 1,2-alkylene-4-substituted urazole of general formula I is suitable for such purposes.

In general it is believed that a biologically active compound causes some interaction with vital tissues to develop various actions. In case of a compound having a herbicidal or weeding activity, it has been appreciated that absorption of chemical and its translocation in plants and the reaction at the site of action are most important factors, which is effected by lipophilic-hydrophilic balance of compound concerned.

It may be considered that the urazole derivatives have a good lipophilic-hydrophilic balance based on introduction of the alkylene chain attached to $N^1$- and $N^2$-positions in cisconfiguration at $N^1$- and $N^2$-positions and electron donating moieties, $N^1$ and $N^2$, instead of a double bond in N-(p-chlorophenyl)-3,4,5,6-tetrahydrophthalimide.

These characters play important role for the appearance of herbicidal activities of the urazole derivatives according to this invention.

Among the compounds listed in Tables V, VI and VII, following compounds may be used as active herbicidal ingredient.

URAZOLE DERIVATIVE 1,2-tetramethylene-4-(4'-chlorophenyl)urazole,
1,2-tetramethylene-4-(4'-bromophenyl)urazole,
1,2-tetramethylene-4-(4'-iodophenyl)urazole,
1,2-tetramethylene-4-(4'-fluorophenyl)urazole,
1,2-tetramethylene-4-[4'-(4''-chlorobenzyloxy)phenyl]urazole,
1,2-tetramethylene-4-(3'-methyl-4'-chlorophenyl)urazole,
1,2-tetramethylene-4-(3'-methyl-4'-bromophenyl)urazole,
1,2-tetramethylene-4-(3',4'-dichlorophenyl)urazole,
1,2-tetramethylene-4-(4'-methoxyphenyl)urazole,
1,2-trimethylene-4-(4'-chlorophenyl)urazole,
1,2-trimethylene-4-(4'-bromophenyl)urazole,
1,2-trimethylene-4-[4'-(4''-chlorobenzyloxy)phenyl]urazole,
1,2-trimethylene-4-(3',4'-dichlorophenyl)urazole,
1,2-trimethylene-4-(4'-methoxyphenyl)urazole,
1,2-tetramethylene-4-(4'-nitrophenyl)urazole,
1,2-tetramethylene-4-(3'-bromo-4'-methylphenyl)urazole,
1,2-tetramethylene-4-(3',4'-dimethylphenyl)urazole,
1,2-tetramethylene-4-(4'-methylphenyl)urazole,
1,2-tetramethylene-4-(4'-ethoxyphenyl)urazole,
1,2-pentamethylene-4-(4'-chlorophenyl)urazole,
1,2-pentamethylene-4-(4'-bromophenyl)urazole,
1,2-pentamethylene-4-[4'-(4''-chlorobenzyloxy)phenyl]urazole,
1,2-pentamethylene-4-(3',4'-dichlorophenyl)urazole,
1,2-pentamethylene-4-(4'-methoxyphenyl)urazole,
1,2-tetramethylene-4-(3'-chlorophenyl)urazole,
1,2-tetramethylene-4-(3'-bromophenyl)urazole,
1,2-tetramethylene-4-(3'-trifluoromethylphenyl)urazole,
1,2-tetramethylene-4-(4'-n-buthoxyphenyl)urazole,
1,2-tetramethylene-4-(3',5'-dichlorophenyl)urazole,
1,2-(1''-methyl trimethylene)-4-(4'-chlorophenyl)urazole,
1,2-(1''-methyl tetramethylene)-4-(4'-chlorophenyl)urazole,
1,2-(2''-methyl tetramethylene)-4-(4'-chlorophenyl)urazole,
1,2-trimethylene-4-(4'-nitrophenyl)urazole,
1,2-trimethylene-4-(4'-methylphenyl)urazole,
1,2-trimethylene-4-(3'-trifluoromethylphenyl)urazole,
1,2-pentamethylene-4-(4'-nitrophenyl)urazole,
1,2-pentamethylene-4-(4'-methylphenyl)urazole,
1,2-pentamethylene-4-(3'-trifluoromethylphenyl)urazole,
1,2-hexamethylene-4-(4'-chlorophenyl)urazole,
1,2-ethylene-4-(4'-chlorophenyl)urazole,
1,2-trimethylene-4-(3',5'-dichlorophenyl)urazole,
1,2-(1''-methyl trimethylene)-4-(3',5'-dichlorophenyl)urazole,
1,2-(1''-methyl tetramethylene)-4-(3',5'-dichlorophenyl)urazole,
1'',2-(2''-methyl tetramethylene)-4-(3',5'-dichlorophenyl)urazole,
1,2-(1'',4''-dimethyl tetramethylene)-4-(3',5'-dichlorophenyl)urazole,
1,2-(2'',3''-dimethyl tetramethylene)-4-(3',5'-dichlorophenyl)urazole,
1,2-pentamethylene-4-(3',5'-dichlorophenyl)urazole,
1,2-hexamethylene-4-(3',5'-dichlorophenyl)urazole,
1,2-octamethylene-4-(3',5'-dichlorophenyl)urazole,
1,2-(1''',4''-dimethyl tetramethylene)-4-(4'-chlorophenyl)urazole,
1,2-(2'',3''-dimethyl)tetramethylene)-4-(4'-chlorophenyl)urazole,
1,2-tetramethylene-4-(4'-t-butylphenyl)urazole,
1,2-tetramethylene-4-(1'-naphthyl)urazole,
1,2-tetramethylene-4-(2'-methylphenyl)urazole and
1,2-tetramethylene-4-(3'-methylphenyl)urazole.

MONOTHIOURAZOLE DERIVATIVES 1,2-tetramethylene-4-(4'-chlorophenyl)monothiourazole,
1,2-tetramethylene-4-(4'-bromophenyl)monothiourazole,
1,2-tetramethylene-4-(4'-iodophenyl)monothiourazole,
1,2-tetramethylene-4-(4'-fluorophenyl)monothiourazole,
1,2-tetramethylene-4-[4'-(4''-chlorobenzyloxy)phenyl]-monothiourazole,
1,2-tetramethylene-4-(3',4'-dichlorophenyl)monothiourazole,
1,2-tetramethylene-4-(3'-methyl-4'-chlorophenyl)monothiourazole,
1,2-tetramethylene-4-(3'-methyl-4'-bromophenyl)monothiourazole,
1,2-tetramethylene-4-(4'-nitrophenyl)monothiourazole,
1,2-tetramethylene-4-(4'-methoxyphenyl)monothiourazole,
1,2-trimethylene-4-(4'-chlorophenyl)monothiourazole,
1,2-trimethylene-4-(4'-methoxyphenyl)monothiourazole,
1,2-pentamethylene-4-(4'-chlorophenyl)monothiourazole,
1,2-pentamethylene-4-(4'-bromophenyl)monothiourazole,
1,2-pentamethylene-4-(4'-methoxyphenyl)monothiourazole,
1,2-tetramethylene-4-(4'-methylphenyl)monothiourazole,
1,2-tetramethylene-4-(4'-ethoxyphenyl)monothiourazole,
1,2-tetramethylene-4-(3'-chlorophenyl)monothiourazole,
1,2-tetramethylene-4-(3'-bromophenyl)monothiourazole,
1,2-tetramethylene-4-(3',4'-dimethylphenyl)monothiourazole,
1,2-tetramethylene-4-(3',5'-dichlorophenyl)monothiourazole,
1,2-tetramethylene-4-(3'-methylphenyl)monothiourazole, 1,2-tetramethylene-4-(3'-trifluoromethylphenyl)monothiourazole,
1,2-trimethylene-4-(4'-methylphenyl)monothiourazole,
1,2-trimethylene-4-(3',5'-dichlorophenyl)monothiourazole,
1,2-pentamethylene-4-(4'-methylphenyl)monothiourazole,
1,2-pentamethylene-4-(3',5'-dichlorophenyl)monothiourazole,
1,2-(2'',3''-dimethyl tetramethylene)-4-(4'-chlorophenyl)monothiourazole,
1,2-hexamethylene-4-(4''-chlorophenyl)monothiourazole,
1,2-hexamethylene-4-(4'-methoxyphenyl)monothiourazole,
1,2-tetramethylene-4-methylmonothiourazole,
1,2-tetramethylene-4-ethylmonothiourazole,
1,2-tetramethylene-4-allylmonothiourazole,
1,2-tetramethylene-4-cyclohexylmonothiourazole,
1,2-tetramethylene-4-(4'-n-butylphenyl)monothiourazole,
1,2-tetramethylene-4-(2',6'-diethylphenyl)monothiourazole,
1,2-tetramethylene-4-(2'-methylphenyl)monothiourazole and
1,2-tetramethylene-4-(1'-naphthyl)monothiourazole.

DITHIOURAZOLE DERIVATIVES 1,2-tetramethylene-4-(4'-chlorophenyl)dithiourazole,
1,2-tetramethylene-4-(4'-bromophenyl)dithiourazole,
1,2-tetramethylene-4-(4'-iodophenyl)dithiourazole,
1,2-tetramethylene-4-(4'-fluorophenyl)dithiourazole,
1,2-tetramethylene-4-(3'-methyl-4'-chlorophenyl)dithiourazole,
1,2-tetramethylene-4-(3'-methyl-4'-bromophenyl)dithiourazole,
1,2-tetramethylene-4-(3',4'-dichlorophenyl)dithiourazole,
1,2-tetramethylene-4-(4'-methoxyphenyl)dithiourazole,
1,2-tetramethylene-4-(4'-nitrophenyl)dithiourazole,
1,2-(2''-butenylene)-4-(4'-chlorophenyl)dithiourazole,
1,2-trimethylene-4-(4'-chlorophenyl)dithiourazole,
1,2-pentamethylene-4-(4'-chlorophenyl)dithiourazole,
1,2-(2''-methyl tetramethylene)-4-(4'-chlorophenyl)dithiourazole,
1,2-tetramethylene-4-(4'-methylphenyl)dithiourazole,
1,2-tetramethylene-4-(3'-chlorophenyl)dithiourazole,
1,2-tetramethylene-4-(3'-bromophenyl)dithiourazole,
1,2-tetramethylene-4-(3',4'-dimethylphenyl)dithiourazole,
1,2-hexamethylene-4-(4'-chlorophenyl)dithiourazole,
1,2-tetramethylene-4-(3',5'-dichlorophenyl)dithiourazole,
1,2-tetramethylene-4-(3'-methylphenyl)dithiourazole and
1,2-tetramethylene-4-(3'-trifluoromethylphenyl)dithiourazole.

By the more detailed results, the position of substituents on phenyl ring attached to $N^4$-position in the urazole ring may give a great influence on the herbicidal activity.

Especially, the compounds which have halogen, lower alkyl, lower alkoxy or halogenobenzyloxy on para-position of the phenyl ring show excellent herbicidal activities.

3,4-Dihalogenophenyl compounds and 3-alkyl-4-halogenophenyl compounds show also strong activities.

The active compound according to this invention is formulated into a herbicide by diluting it with an inert carrier in liquid or solid and, if desired, incorporating a surface active agent to obtain a herbicide in the form of a dust, emulsion, wettable powder or granule. If necessary, it is possible to add one or more other active ingredients, such as fungicide, insecticide, nematocide, fertiliser, synergetic agent, another herbicide or plant growth regulator.

Examples of liquid medium which may be used in this invention include various solvents, for example, a hydrocarbon such as kerosene, benzene and xylene, a halogenated hydrocarbon such as chlorobenzene and dichloroethylene, a lower alcohol such as ethanol and a ketone such as acetone. Examples of solid carrier are, for example, bentonite, kaoline, clay, talc, activated clay, diatomaceous earth, siliceous sand and calcium carbonate.

As surface active agent which may be used for formulating the herbicidal composition according to this invention, there are exemplified alkylbenzene sulfonate, lignosulfonate, sulfate ester of higher alcohol, of polyoxyethylene aliphatic ester, polyoxyethylene sorbitane aliphatic ester, dialkyl sulfosuccinate and alkyltrimethyl ammonium chloride.

The dosage rate of the compound according to this invention to be applied as active ingredient is not critical so far as intended herbicidal activity is achieved; however, it is preferable, in general, that 5 to 50 g of the compound be applied per 100 $m^2$.

It is proved from tests given hereinafter that herbicide according to this invention shows by foliage or soil treatment excellent herbicidal activity against various weeds at germinating and growing stages.

Embodiments of formulation of the herbicide according to this invention are illustrated by way of Example; the number of the compound employed corresponds to the compound number in Tables 1, 2 and 3 and "part" and "percentage" given therein are by weight unless otherwise defined.

EXAMPLE 1 (Emulsifiable oil)

Thirty parts of compound No. 1 was dissolved in a mixed solvent of 30 parts of xylene and 25 parts of N,N-dimethylformamide, and 15 parts of surface active agent available from Toho Chemical Industries Limited, Tokyo, Japan under name of Solpole 900A was added to the solution to formulate an emulsion containing 30% of the active ingredient.

EXAMPLE 2 (Wettable powder)

A mixture of 50 parts of compound No. 6, 45 parts of diatomaceous earth and 5 parts of surface active agent, Solpole 8070 available from Toho Chemical Industries Limited, was thoroughly ground to obtain a wettable powder containing 50% of the active ingredient.

EXAMPLE 3 (Granule)

Water was added to a mixture of 5 parts of compound No. 12, 66 parts of talc, 27 parts of bentonite and 2 parts of Aerole CT-1, surface active agent available from Toho Chemical Industries Limited, with kneading. The paste thus obtained was processed with a granulating machine and dried at 60° C. for two hours to give a granule containing 5% of the active ingredient.

EXAMPLE 4 (Emulsifiable oil)

A solution of 20 parts of compound No. 60 in 70 parts of mixed solvent comprised of equal amount by weight of N,N-dimethylformamide and Kawakasol, an organic solvent available from Kawasaki Chemical Industries Limited, Tokyo, Japan, was mixed with 10 parts of Solpole 9838 to obtain an emulsion.

EXAMPLE 5 (Wettable powder)

A wettable powder was formulated by mixing and grinding 50 parts of compound No, 51, 45 parts of diatomaceous earth and 5 parts of Solpole 8070.

EXAMPLE 6

A solution of 30 parts of compound No. 43 in a mixed solvent of 30 parts of N,N-dimethylformamide and 35 parts of xylene was mixed with 5 parts of polyoxyethylene naphthylethersulfonate to give an emulsion containing 30% of the active ingredient.

EXAMPLE 7 (Wettable powder)

A wettable powder containing 50% of active ingredient was formulated by mixing and grinding 50 parts of compound No. 95, 10 parts of diatomaceous earth, 35 parts of kaoline and 5 parts of sodium dodecylbenzenesulfonate.

EXAMPLE 8 (Granule)

A mixture of 5 parts of compound No. 18, 27 parts of diatomaceous earth, 66 parts of bentonite and 2 parts of Aerole CT-1 was kneaded with water and granulated. The resulting granules were dried at 60° C. for 2 hours to obtain a herbicide containing 5% of the active ingredient.

The preparation of the compound according to this invention will be explained by way of Example. It should be understood that this invention is not limited by such Examples. The letter shown in parenthesis after the Example number shows the Route employed.

EXAMPLE 9 (A)

Thirty milliliters of methanol containing 0.46 g of sodium was mixed with 2.12 g of 4-(4'-chlorophenyl-)urazole and after a while methanol was distilled off from the mixture. To the residue were added 30 ml of N,N-dimethylformamide and 2.4 g of tetramethylene bromide, then the mixture was heated under reflux condition for one hour with agitation. Then, precipitated sodium bromide was separated by filtration. The filtrate was concentrated in vacuo and diluted with water to precipitate crystals which were collected by filtration, the yield of crude being 98%. After recrystallization from ethanol, 2.2 g of 4-(4'-chlorophenyl)-1,2-tetramethyleneurazole having a melting point of 192.0°-192° C. was obtained, the yield being 83%.

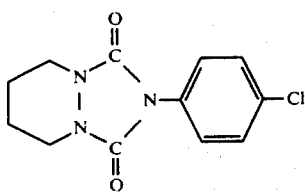

The elementary analysis as $C_{12}H_{12}O_2N_3Cl$ was:

|  | C% | H% | N% | Cl% |
|---|---|---|---|---|
| Calculation | 52.24 | 4.55 | 15.82 | 13.35 |
| Found | 54.38 | 4.40 | 15.91 | 13.33 |

EXAMPLE 10 (A)

The procedures of Example 9 were repeated but using 0.8 g of potassium instead of the sodium to obtain 1.95 g of 4-(4'-chlorophenyl)-1,2-tetramethyleneurazole (yield being 73%). The melting point and the elementary analysis of the product were substantially identical with those of Example 9.

EXAMPLE 11 (A)

A solution of 0.01 mole each of 4-substituted phenylurazole derivatives listed in Table 1 in 30 ml of N,N-dimethylformamide was mixed with 0.01 mole each of salt-forming bases listed in Table 1 to form an urazole salt. After one millimole of tetramethylene bromide was added to the mixture containing the salt, the resulting mixture was heated for one hour under reflux with agitation and treated as Example 9 to obtain 1,2-tetramethylene-4-substituted phenylurazoles.

Each product was identified by means of the melting point and infrared spectrum.

The results are given in Table 1.

TABLE 1

| X' | Salt forming agent | Yield (%) |
|---|---|---|
| 4'-Cl | KOH | 88 |
| 4'-Br | KOH | 83 |
| 3',4'-Cl$_2$ | KOH | 92 |
| 4'-Cl | NaOH | 75 |
| " | CH$_3$ONa | 80 |
| " | NaH | 84 |
| " | NaNH$_2$ | 79 |
| " | (C$_2$H$_5$)$_3$N | 65 |
| " | NH$_3$ | 55 |
| " | Pyridine | 42 |
| " | Ba(OH)$_2$ . 8H$_2$O | 83 |

EXAMPLE 12 (A)

The procedures in Example 10 were repeated excepting that instead of N,N-dimethyl formamide, the various solvents given in Table 2 were used to produce 4-(4'-chlorophenyl)-1,2-tetramethyleneurazole. The results are given in Table 2.

| Solvent | Yield of the product (%) |
|---|---|
| Dimethyl sulfoxide | 91 |
| Dimethylacetamide | 84 |
| N-methyl pyrolidone | 86 |
| Sulfolane | 90 |
| Hexamethyl phosphoric triamide | 93 |

EXAMPLE 13 (A)

In this Example, the procedures in Example 9 were repeated but the cycloalkylation conditions including the halogenide and reaction temperature and time were changed as given in Table 3.

TABLE 3

|  | Temp. | Time (hr) | Yield (%) |
|---|---|---|---|
| BrCH$_2$CH$_2$CH$_2$CH$_2$Br | 100° C. | 1 | 72 |
| " | 25° C. | 1 | 15 |
| ICH$_2$CH$_2$CH$_2$CH$_2$I | under reflux | 1 | 88 |
| " | 100° C. | 1 | 85 |
| " | 25° C. | 3 | 47 |

EXAMPLE 14 (A)

A mixture of 0.01 mole of a 4-substituted phenylurazole derivative, 0.02 mole of a salt-forming base, 30 ml of a solvent and 0.01 mole of tetramethylene bromide was heated under reflux for one hour followed by distilling off the solvent and adding water to the residue to precipitate crystals which were filtered.

The results as well as starting materials and solvents are given in Table 4.

TABLE 4

| X' | Solvent | Salt forming agent | Yield (%) |
|---|---|---|---|
| 4'-Cl | C$_2$H$_5$OH | C$_2$H$_5$ONa | 63 |
| 4'-OCH$_3$ | " | " | 61 |
| 4'-Cl | C$_2$H$_5$OH | KOH | 49 |
| " | Dioxane-H$_2$O (4:1) | " | 58 |
| " | Dioxane-H$_2$O (2:1) | " | 43 |
| " | Toluene | C$_2$H$_5$ONa | 12 |

EXAMPLE 15 (A)

A solution of 0.01 mole of 4-(4'-chlorophenyl)urazole in 30 ml of acetone, 0.02 mole of potassium carbonate, 0.001 mole of potassim iodide and 0.01 mole of tetramethylene halide (bromide or chloride) were mixed and heated under reflux for 5 hours, and the reaction mixture was poured into a substantial amount of water to precipitate 4-(4'-chlorophenyl)-1,2-tetramethyleneurazole. The yield was 66% and 53% where the bromide and chloride were employed, respectively.

Various other 1,2-alkylene-4-aryl urazole derivatives given in Table 5 were synthesized according to the procedures similar to those of Example 9.

EXAMPLE 16(B)

Into a suspension of 4.87 g (0.023 mole) of 4-(4'-chlorophenyl)urazole in 100 ml of dichloromethane was absorbed 1.35 g of 1,3-butadiene. Then a solution of 13.4 g (0.026 mole) of lead tetraacetate in 100 ml of dichloromethane was added dropwise over 30 minutes to the reaction mixture prepared as above was maintained with agitation at a temperature of 0° to 5° C. in an ice bath, and after continuing agitation for an additional two hours at that temperature, dichloromethane was distilled off in vacuo at a temperature below 40° C.

The residue was washed in sequence with each 75 ml of water, 0.1 N nitric acid, 0.1 N sodium hydroxide and water, and recrystallized from ethylacetate to obtain 4.3 g of 1,2-(2''-butenylene)-4-(4'-chlorophenyl)urazole (yield being 71%).

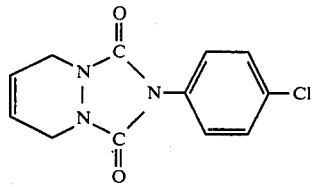

The melting point was 176°–177° C. and the elementary analysis as C$_{12}$H$_{16}$O$_2$N$_3$Cl was:

|  | C % | H % | N % | Cl % |
|---|---|---|---|---|
| Calculation | 54.66 | 3.82 | 15.94 | 13.45 |
| Found | 54.40 | 3.70 | 15.71 | 13.31 |

EXAMPLE 17(B)

To a suspension of 5.3 g (0.025 mole) of 4-(4'-chlorophenyl)urazole in 12 ml of ethyl acetate was added 2.5 g of t-butyl hypochlorite over 20 minutes with agitation under nitrogen stream and then the reaction mixture was agitated for 40 minutes at room temperature to complete the reaction. After distilling off the solvent at a temperature below 40° C. in vacuo, the resulting crude 4-(4'-chlorophenyl)-1,2,4-triazoline-3,5-dione was dissolved in 30 ml of acetone and, upon adding 1.64 g of 2,4-hexadiene to the solution which was maintained at a temperature of −50° C. under nitrogen stream, the reaction was instantaneously completed.

The solvent was removed from the reaction mixture by evaporation in vacuo at a temperature below 40° C. and the solid material recovered was recrystallized from methanol-water to obtain 1,2-(1'',4''-dimethyl-2''-butenylene)-4-(4'-chlorophenyl) urazole having a melting point of 147°–148.5° C. in an amount of 2.3 g (the yield being 40%).

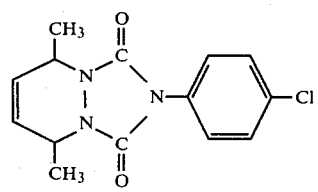

The elementary analysis as C$_{14}$H$_{14}$O$_2$N$_3$Cl was:

|  | C % | H % | N % | Cl % |
|---|---|---|---|---|
| Calculation | 57.63 | 4.84 | 14.41 | 12.15 |
| Found | 57.85 | 4.68 | 14.59 | 12.11 |

Following the procedures of Examples 17 and 16, there were synthesized the following compounds:

|  | Melting point (°C.) |
|---|---|
| 1,2-(2″-butenylene)-4-(4′-methylphenyl)urazole | 175-7 |
| 1,2-(2″-butenylene)-4-(4′-nitrophenyl)urazole | 267-8 |
| 1,2-(2″-butenylene)-4-(4′-chlorophenyl)urazole | 176-7 |
| 1,2-(2″-butenylene) 4-(3′,4′-dichlorophenyl)urazole | 233-5 |
| 1,2-(2″-butenylene)-4-(4′-fluorophenyl)urazole | 186-8 |
| 1,2-(2″-butenylene)-4-(4′-bromophenyl)urazole |  |
| 1,2-(2″-butenylene)-4-(3′-trifluoromethylphenyl)urazole |  |
| 1,2-(2″-butenylene)-4-(4′-methoxyphenyl)urazole | 153-4 |
| 1,2-(2″-butenylene)-4-(3′,5′-dichlorophenyl)urazole | 167-8 |
| 1,2-(1″-methyl-2″-butenylene)-4-(2′-, 3′- or 4′-methylphenyl)urazole |  |
| 1,2-(1″-methyl-2″-butenylene)-4-(4′-methoxyphenyl)urazole |  |
| 1,2-(1″-methyl-2″-butenylene)-4-(4′-chlorophenyl)urazole | 128-31 |
| 1,2-(1″-methyl-2″-butenylene)-4-(3′, 5′-dichlorophenyl)urazole | 151-3 |
| 1,2-(1″-methyl-2″-butenylene)-4-(4′-fluorophenyl)urazole |  |
| 1,2-(1″-methyl-2″-butenylene)-4-(4′-bromophenyl)urazole |  |
| 1,2-(2″-methyl-2″-butenylene)-4-(2′-, 3′- or 4′-methylphenyl)urazole |  |
| 1,2-(2″-methyl-2″-butenylene)-4-(4′-methoxyphenyl)urazole |  |
| 1,2-(2″-methyl-2″-butenylene)-4-(4′-chlorophenyl)urazole | 157-9.5 |
| 1,2-(2″-methyl-2″-butenylene)-4-(3′-, 5′-dichlorophenyl)urazole | 193-4 |
| 1,2-(2″-methyl-2″-butenylene)-4-(4′-fluorophenyl)urazole |  |
| 1,2-(2″-methyl-2″-butenylene)-4-(4′-bromophenyl)urazole |  |
| 1,2-(2″-,3″-dimethyl-2″-butenylene)-4-(3′- or 4′-methylphenyl)urazole |  |
| 1,2-(2″-,3″-dimethyl-2″-butenylene)-4-(4′-methoxyphenyl)urazole |  |
| 1,2-(2″,3″-dimethyl-2″-butenylene)-4-(4′-chlorophenyl)urazole | 178-80 |
| 1,2-(2″,3″-dimethyl-2″-butenylene)-4-(3′,5′-dichlorophenyl)urazole | 370 |
| 1,2-(2″-3″-dimethyl-2″-butenylene)-4-(4′-fluorophenyl)urazole |  |
| 1,2-(2″,3″-dimethyl-2″-butenylene)-4-(4′-bromophenyl)urazole |  |
| 1,2-(1″,4″-dimethyl-2″-butenylene)-4-(2′-, 3′- or 4′-methylphenyl)urazole |  |
| 1,2-(1″,4″-dimethyl-2″-butenylene)-4-(4′-chlorophenyl)urazole | 147-8.5 |
| 1,2-(1″,4″-dimethyl-2″-butenylene)-4-(4′-methoxyphenol)urazole |  |
| 1,2-(1″,4″-dimethyl-2″-butenylene)-4-(4′-bromophenyl)urazole | 231-3 |
| 1,2-(1″,4″-dimethyl-2″-butenylene)-4-(3′-,5′-dichlorophenyl)urazole. |  |

EXAMPLE 18(B)

To a solution of 2.63 g of 1,2-(2″-butenylene)-4-(4′-chlorophenyl)urazole in 100 ml of ethyl acetate was added 100 mg of a catalyst of 5% palladium supported on carbon and 250 ml of hydrogen was absorbed in the reaction mixture prepared as above. After separating the catalyst by filtration, the solvent was removed by distillation in vacuo to obtain in a quantitative amount of 1,2-tetramethylene-4-(4′-chlorophenyl)urazole having a melting point of 192.0°-193.0° C.

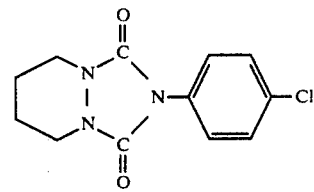

Repeating the procedures of this Example, compounds Nos. 1, 2, 7 to 9, 11, 14, 43, 44, 46, 48 and 50 in Table 5 were prepared.

EXAMPLE 19(B)

Hydrogen was passed through at a temperature of 25° C. a mixture of 2.92 g of 1,2-(2″,3″-dimethyl-2′-butenylene)-4-(4′-chlorophenyl)urazole, 100 ml of glacial acetic acid and 100 mg of platinum oxide catalyst to effect hydrogenation, the amount of hydrogen absorbed being 250 ml. After separating the catalyst by filtration, acetic acid was removed by distillation in vacuo and the residual material was recrystallized from ethanol-ethyl acetate to obtain following 1,2-(2″,3″-dimethyl tetramethylene)-4-(4′-chlorophenyl)urazol having a melting point 174.5°-175.5° C. in an amount of 2.65 g, the yield being 90%.

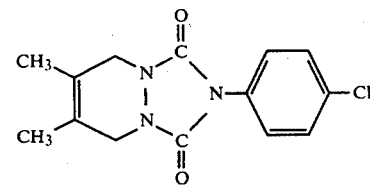

The elementary analysis thereof is given in Table 5.

EXAMPLE 20(B)

The procedures similar to those of Example 18 were repeated but the solvent was methanol, then from 2.92 g of 1,2-(1″,4″-dimethyl-2″-butenylene)-4-(4′-chlorophenyl)urazole a quantitative amount of 1,2-(1″,4″-dimethyl-tetramethylene)-4-(4′-chlorophenyl)urazole was prepared, the melting point being 165.0°-167.5° C.

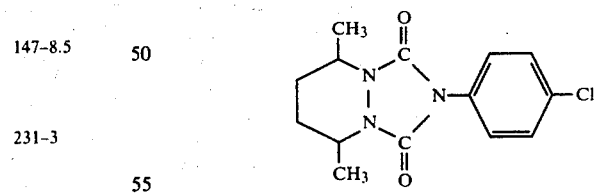

According to the procedures of this Example, compounds Nos. 3 and 4 in Table 5 were also produced.

EXAMPLE 21(B)

Into a 300 ml capacity autoclave were charged a solution of 2.78 g of 1,2-(2″-methyl-2″-butenylene)-4-(4′-chlorophenyl)urazole in 100 ml of methanol and 100 mg of 10% palladium supported on carbon catalyst, and hydrogen was passed through the content under agitation at a pressure of 30 kg/cm² to effect hydrogenation.

After separating the catalyst by filtration, methanol was distilled off from the filtrate to obtain a quantitative amount of 1,2-(2″-methyl tetramethylene)-4-(4′-chlorophenyl)urazole having a melting point of 160°–162° C.

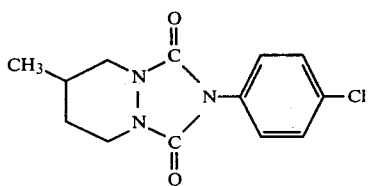

EXAMPLE 22(B)

Hydrogen (250 ml) was absorbed in a solution of 2.59 g of 1,2-(2‴-butenylene)-4-(4″-chlorophenyl)urazole in 150 ml of methanol containing 150 mg of 5% palladium-barium sulfate catalyst.

The catalyst was filtered out and methanol was removed from the filtrate to obtain a solid material which was recrystallized from ethanol. The product weighing 2.20 g and having a melting point of 148°–153° C. was identified as 1,2-tetramethylene-4-(4′-methoxyphenyl)urazole.

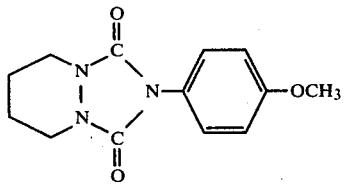

The procedures of this Example were repeated to produce compound No. 13 of Table 5.

EXAMPLE 23(C)

To a solution of 1.58 g (0.01 mole) of 1,2-tetramethylene-1-carbethoxyhydrazine in 25 ml of cumene, 1.80 g (0.01 mole) of p-nitrophenyl isothiocyanate was added in small increments, while the solution was being shaken, there was observed instantaneous precipitation of crystals of 1,2-tetramethylene-1-carbethoxy-2-(4′-nitrophenyl thiocarbamoyl) hydrazine in a quantitative amount. The reaction mixture was heated under reflux condition for 12 hours to effect cyclization.

After allowing to cool, the reaction system was mixed with petroleum ether to precipitate crystals which were separated by filtration and washed with petroleum ether to obtain 1,2-tetramethylene-4-(4′-nitrophenyl) thiourazole weighing 1.78 g, the yield being 95%. After recrystallization from ethanol-benzene mixture, a purified product had a melting point of 168°–169.5° C.

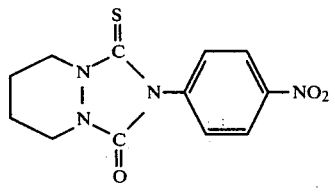

The elementary analysis is given in Table 6.

The same procedures were repeated but 1,2-tetramethylene-1-carbomethoxy hydrazine was used as the starting material, then 1,2-tetramethylene-4-(4′-nitrophenyl) thiourazole was obtained.

EXAMPLE 24(C)

The procedures similar to those of Example 23 were repeated excepting that 1,2-(2′,3′-dimethyl tetramethylene)-1-carbethoxyhydrazine and p-chlorophenyl isothiocyanate as starting materials, and 8 hours of reflux time were employed to obtain 2.94 g (the yield being 95%) of crude 1,2-(2,3-dimethyl tetramethylene)-4-(4′-chlorophenyl) thiourazole. By recrystallization from ethanol, pure colorless needle crystals having a melting point of 239°–241° C. were obtained.

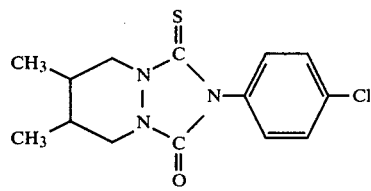

The elementary analysis is given in Table 6.

EXAMPLE 25(C)

A mixture of 3.00 g (0.01 mole) of 1,2-tetramethylene-1-carbomethoxy-2-(p-chlorophenyl thiocarbamoyl) hydrazine, 200 mg of sodium acetate and 40 ml of xylene was heated under reflux for 5 hours with agitation. After distilling off the solvent in vacuo, the precipitated crystals were washed with water and recrystallized from benzene-ethanol to obtain 2.42 g (the yield being 86%) of 1,2-tetramethylene-4-(4′-chlorophenyl) thiourazole. The melting point of the product was 163.5°–165° C.

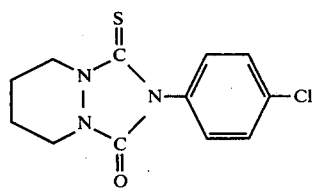

The elementary analysis is given in Table 6.

The same procedures were repeated using 30 mg of sodium ethylate, 100 mg of potassium hydroxide and 300 mg of triethyl amine instead of sodium acetate to obtain the above compound in an yield of 96%, 63% and 75%, respectively.

Similarly, the object compound was also prepared from 1,2-tetramethylene-1-carbethoxy-2-(4′-chlorophenyl thiocarbamoyl) hydrazine.

EXAMPLE 26(C)

Two grams (0.01 mole) of 3,5-dichlorophenyl isothiocyanate was added in small increments to a solution of 1.7 g (0.01 mole) of 1,2-pentamethylene-1-carbethoxy hydrazine with shaking, then 1,2-pentamethylene-1-carbethoxy-2-(3′,4′-dichlorophenyl thiocarbamoyl) hydrazine was instantaneously produced in a quantitative amount. A part of the reaction mixture was sampled and the solvent was removed therefrom to precipitate crystals; then the melting point and elementary analysis thereof were as follow.

Melting point: 128°–130° C.

Elementary analysis as $C_{15}H_{19}Cl_2N_3O_2S$:

|  | C % | H % | N % | Cl % | S % |
|---|---|---|---|---|---|
| Calculation | 47.88 | 5.09 | 11.17 | 18.84 | 8.52 |
| Found | 47.85 | 5.06 | 11.22 | 18.75 | 8.48 |

The reaction mixture containing the product as above was heated under reflux for 8 hours, allowed to cool and diluted with petroleum ether to precipitate crystals which were collected by filtration, washed with petroleum ether and recrystallized from ethanol/benzene to obtain 2.5 g of 1,2-pentamethylene-4-(3′,5′-dichlorophenyl) thiourazole corresponding to a 77% yield.

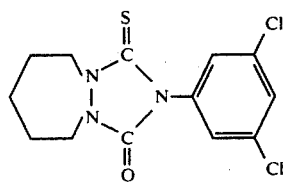

The melting point of the product was 168°–170° C.
The elementary analysis thereof is given in Table 6.

EXAMPLE 27(C)

To a solution of 1.74 g (0.02 mole) of 1,2-tetramethylene-1-thionocarbethoxyhydrazine in 10 ml of chlorobenzene was added 1.70 g (0.01 mole) of p-chlorophenyl isothiocyanate with shaking, then 1,2-tetramethylene-1-thionocarbethoxy-2-(4′-chlorophenyl thionocarbamonyl) hydrazine was instantaneously precipitated. The reaction mixture was heated under reflux for 8 hours, allowed to cool and mixed with petroleum ether to precipitate crystals which were collected by filtration and washed with petroleum ether to obtain 2.83 g of 1,2-tetramethylene-4-(4′-chlorophenyl) dithiourazole (the yield being 95%). The product was purified by recrystallization from ethylacetate/ethanol. The melting point of the object compound was 206°–208° C.

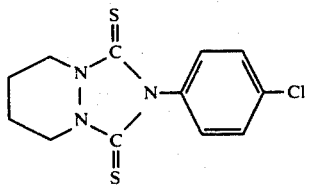

By similar procedures, 1,2-tetramethylene-4-(4′-bromophenyl) dithiourazole was obtained in a yield of 95%.

EXAMPLE 28(C)

Two grams of 3,5-dichlorophenyl isocyanate was added to a solution of 1.74 g of ethyl 1,2-tetramethylenehydrazine-1-dithiocarboxylate in 10 ml of benzene with shaking, then there was observed precipitated crystals of the following compound:

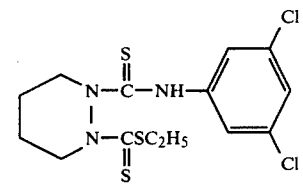

Melting point: 147°–149° C.
Elementary analysis as $C_{14}H_{17}Cl_2N_3S_3$:

|  | C % | H % | N % | Cl % | S % |
|---|---|---|---|---|---|
| Calculation | 42.63 | 4.35 | 10.65 | 17.98 | 24.39 |
| Found | 42.58 | 4.31 | 10.62 | 18.04 | 24.33 |

The reaction mixture containing the crystals was treated as in Example 27 to obtain 2.4 g (the yield being 65%) of 1,2-tetramethylene-4-(3′,5′-dichlorophenyl) dithiourazole.

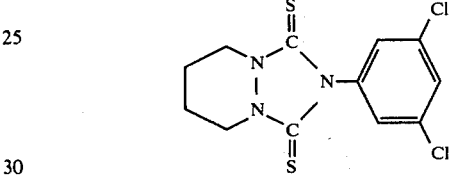

The melting point and the elementary analysis of the purified product recrystallized from ethylacetate ethanol are given in Table 7.

EXAMPLES 29(C) AND (D)

A mixture of 3.3 g (0.01 mole) of 1,2-tetramethylene-1-ethoxycarbonyl-2-(4′-chlorophenyl thiocarbamoyl) hydrazine and 25 ml of cumene was heated under reflux for 8 hours and cooled to room temperature, then 2.22 g (0.01 mole) of phosphorous pentasulfide and 25 ml of cumene were added and the reaction mass was heated under reflux for 5 hours with agitation. After cooling the mass, the precipitated material was filtered off and the filtrate was concentrated in vacuo to obtain a crude product which was recrystallised from ethanol.

The product weighed 2.55 g corresponding to a yield of 85.6% and had a melting point of 206°–208° C.

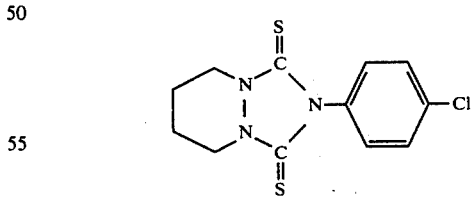

EXAMPLE 30(D)

A mixture of 2.61 g (0.01 mole) of 1,2-tetramethylene-4-(4′-methoxyphenyl)urazole, 2.22 g (0.01 mole) of phosphorous pentasulfide and 50 ml of xylene was heated under reflux for 4 hours with agitation. After cooling the reaction mixture, undissolved material was removed by filtration and the filtrate was concentrated by distillation in vacuo to obtain crystals which were recrystallized from ethanol. The resulting product, 1,2- tetramethylene-4-(4'-methoxyphenyl)thiourazole, weighed 1.71 g (the yield being 62%) and had a melting point of 140°–141° C.

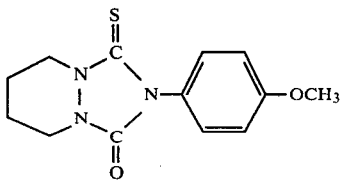

According to the procedures of this Example the following compounds which are also given in Table 6 were prepared in the yields given.

| Compound No. | Yield % |
|---|---|
| 57 | 60 |
| 58 | 72 |
| 66 | 65 |
| 71 | 65 |
| 73 | 75 |
| 74 | 72 |
| 74 | 75 |
| 83 | 70 |
| 84 | 68 |

EXAMPLE 31(D)

In this Example, procedures similar to those of Example 30 were employed but starting material was 1,2-(2',3'-dimethyl tetramethylene)-4-(4'-chlorophenyl)urazole to obtain 1,2-(2',3'-dimethyl tetramethylene)-4-(4'-chlorophenyl)monothiourazole having a melting point of 239°–241° C. with a yield of 61%.

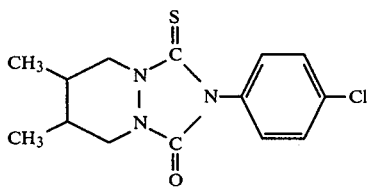

EXAMPLE 32(D)

A mixture of 5.7 g (0.02 mole) of 1,2-trimethylene-4-(3',5'-dichlorophenyl)urazole, 4.4 g (0.02 mole) of phosphorous pentasulfide and 50 ml of xylene was heated under reflux for 4 hours with agitation. After cooling the precipitated solid material was filtered out and the filtrate was concentrated in vacuo to obtain crystals which were recrystallized from ethanol. The product was 1,2-trimethylene-4-(3',5'-dichlorophenyl) monothiourazole weighing 2.5 g (the yield being 41%) and having a melting point of 164°–165.5° C.

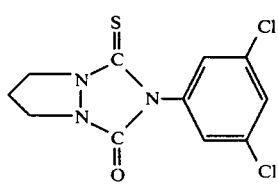

EXAMPLE 33(D)

A mixture of 2.8 g (0.01 mole) of 1,2-(2'-methyl tetramethylene)-4-(4'-chlorophenyl)urazole, 4.44 g (0.02 mole) of phosphorous pentasulfide and 60 ml of xylene was heated under reflux for 8 hours with agitation. After cooling the reaction mixture, undissolved material was filtered off and the filtrate was concentrated in vacuo to precipitate crystals which were recrystallized from ethanol to obtain 2.62 g (the yield being 84%) of 1,2-(2-methyl tetramethylene)-4-(4'-chlorophenyl) dithiourazole having a melting point of 213°–216° C.

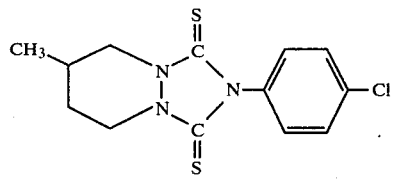

EXAMPLE 34(D)

A mixture of 2.64 g (0.01 mole) of 1,2-(2"-butenylene)-4-(4'-chlorophenyl)urazole, 4.44 g (0.02 mole) of phosphorous pentasulfide and 60 ml of xylene was heated under reflux for 8 hours with agitation. After cooling the reaction mixture, undissolved solid material was separated by filtration and filtrate was concentrated by distillation in vacuo to precipitate crystals which were recrystallized from ethanol to obtain 1.56 g (the yield being 60%) of the desired product having a melting point of 207°–209° C.

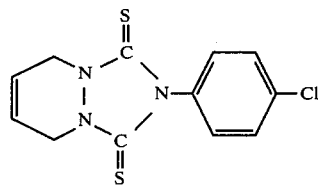

EXAMPLE 35(D)

A mixture of 2.66 g (0.01 mole) of 1,2-tetramethylene-4-(4'-chlorophenyl)thiourazole, 2.22 g (0.01 mole) of phosphorous pentasulfide and 60 ml of toluene was heated under reflux for 7 hours with agitation. After cooling, precipitated material was filtered off and the filtrate was concentrated in vacuo to recover solid material which was recrystallized from ethanol-ethyl acetate to obtain 2.64 g (the yield being 88%) of desired product, 1,2-tetramethylene-4-(4'-chlorophenyl)dithiourazole, the melting point being 206°–208° C.

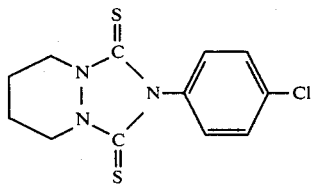

EXAMPLE 36(E)

To a mixture of 60 ml of ethanol and 2 ml of aqueous solution containing 0.66 g of porassium hydroxide was added 2.56 g of 1,2-tetramethylene-1-(p-chlorophenyl thiocarbamoyl) hydrazine and 0.8 g of carbon disulfide, the resulting reaction system was heated under reflux for 3 hours with agitation and the solvent was removed by distillation in vacuo to obtain the solid material which was poured into diluted hydrochloric acid. Undissolved material was separated by filtration, washed with water and recrystallized from ethanol-ethyl acetate to obtain 2.2 g (the yield being 75%) of 1,2-tetramethylene-4-(4'-chlorophenyl) dithiourazole, the melting point being 206°–208° C.

By repeating procedures similar to those of this Example, following compounds given in Table 7 were prepared in the yields given below.

| Compound No. | Yield % |
|---|---|
| 94 | 63 |
| 95 | 75 |
| 96 | 80 |
| 98 | 78 |
| 100 | 81 |
| 101 | 75 |
| 102 | 70 |
| 103 | 72 |

By similar procedures, 1,2-tetramethylene-4-isopropyl dithiourazole and 1,2-tetramethylene-4-cyclohexyl dithiourazole were also prepared.

TABLE 5

| Compd. No. | Structure | Melting point (°C.) | Elementary analysis (%) C | H | N | X | Yield (%) |
|---|---|---|---|---|---|---|---|
| 1 | (structure with phenyl) | 172.5~174 | 63.66 / 63.69 | 6.16 / 6.15 | 17.13 / 17.18 | | 72 |
| 2 | (structure with m-CH₃ phenyl) | 136~138 | 63.66 / 63.65 | 6.16 / 6.20 | 17.13 / 17.10 | | 76 |
| 3 | (structure with p-CH₃ phenyl) | 173.5~175 | 63.66 / 63.81 | 6.16 / 6.11 | 17.13 / 17.21 | | 89 |
| 4 | (structure with p-t-C₄H₉ phenyl) | 186~189 | 66.87 / 66.89 | 7.37 / 7.31 | 14.62 / 14.60 | | 82 |
| 5 | (structure with m-Cl phenyl) | 129~130 | 54.24 / 54.35 | 4.55 / 4.42 | 15.82 / 15.80 | X = Cl 13.35 / 13.21 | 77 |
| 6 | (structure with p-Cl phenyl) | 192~193 | 54.24 / 54.38 | 4.55 / 4.40 | 15.82 / 15.91 | X = Cl 13.35 / 13.33 | 93 |
| 7 | (structure with 3,4-diCl phenyl) | 182~185 | 48.02 / 48.30 | 3.69 / 3.51 | 14.00 / 13.88 | X = Cl 23.63 / 23.59 | 95 |

TABLE 5-continued

| Compd. No. | Structure | Melting point (°C.) | Elementary analysis (%) C | H | N | X | Yield (%) |
|---|---|---|---|---|---|---|---|
| 8 | (3,5-dichlorophenyl derivative) | 139~144 | 42.02 48.27 | 3.69 3.60 | 14.00 13.99 | X = Cl 23.63 23.51 | 92 |
| 9 | (4-bromophenyl derivative) | 180~183 | 46.47 46.52 | 3.90 3.88 | 13.55 13.52 | X = Br 25.77 25.51 | 89 |
| 10 | (4-iodophenyl derivative) | 217~219 | 40.35 40.42 | 3.39 3.37 | 11.77 11.79 | | 88 |
| 11 | (4-fluorophenyl derivative) | 175~178 | 57.82 57.80 | 4.85 4.81 | 16.86 16.81 | | 89 |
| 12 | (4-OCH₃ phenyl derivative) | 148~153 | 59.76 59.85 | 5.79 5.51 | 16.08 15.97 | | 90 |
| 13 | (4-OC₂H₅ phenyl derivative) | 179.5~182 | 61.08 61.00 | 6.22 6.25 | 15.26 15.41 | | 86 |
| 14 | (3-CF₃ phenyl derivative) | 141~143 | 52.18 52.41 | 4.04 4.22 | 14.04 14.00 | | 86 |
| 15 | (4-OC₄H₉-n phenyl derivative) | 118~119.5 | 63.35 63.50 | 6.98 6.90 | 13.85 13.81 | | 83 |
| 16 | (4-NO₂ phenyl derivative) | 225~227 | 52.17 52.00 | 4.38 4.11 | 20.28 20.08 | | 89 |

TABLE 5-continued

| Compd. No. | Structure | Melting point (°C.) | Elementary analysis (%) C | H | N | X | Yield (%) |
|---|---|---|---|---|---|---|---|
| 17 | (structure: bicyclic diketo-triazine with 1-naphthyl) | 200~203 | 68.31 68.29 | 5.38 5.35 | 14.94 14.89 | | 84 |
| 18 | (structure: bicyclic diketo-triazine with 4-(4-chlorobenzyloxy)phenyl) | 161~162 | 61.38 61.19 | 4.88 4.76 | 11.30 11.41 | X = Cl 9.53 9.57 | 85 |
| 19 | (structure: bicyclic diketo-triazine with 4-Cl phenyl, smaller ring) | >280 | 50.54 50.81 | 3.39 3.22 | 17.68 17.89 | X = Cl 14.92 15.11 | 21 |
| 20 | (structure: bicyclic diketo-triazine with 4-CH₃ phenyl) | 167.5~169 | 62.32 62.30 | 5.67 5.69 | 18.17 18.29 | | 74 |
| 21 | (structure: bicyclic diketo-triazine with 4-Cl phenyl) | 157~159 | 52.49 52.61 | 4.01 4.00 | 16.70 16.71 | X = Cl 14.09 14.22 | 78 |
| 22 | (structure: bicyclic diketo-triazine with 4-Br phenyl) | 188~189 | 44.61 44.65 | 3.40 3.46 | 14.19 14.25 | X = Br 26.99 26.71 | 78 |
| 23 | (structure: bicyclic diketo-triazine with 3,4-diCl phenyl) | 176~179 | 46.17 46.21 | 3.17 3.18 | 14.69 14.69 | X = Cl 24.79 24.77 | 80 |
| 24 | (structure: bicyclic diketo-triazine with 3,5-diCl phenyl) | 142~143.5 | 46.17 46.00 | 3.17 3.09 | 16.69 16.34 | X = Cl 24.78 24.56 | |
| 25 | (structure: bicyclic diketo-triazine with 4-OCH₃ phenyl) | 156.5~157.5 | 58.29 58.30 | 5.30 5.22 | 17.00 17.21 | | 77 |

TABLE 5-continued

| Compd. No. | Structure | Melting point (°C.) | Elementary analysis (%) C | H | N | X | Yield (%) |
|---|---|---|---|---|---|---|---|
| 26 | (bicyclic triazine-dione with 4-NO$_2$-phenyl) | 213~215 | 50.38 / 50.48 | 3.84 / 3.83 | 21.37 / 21.27 | | 82 |
| 27 | (bicyclic triazine-dione with 3-CF$_3$-phenyl) | 99~100 | 50.53 / 50.76 | 3.53 / 3.58 | 14.73 / 14.59 | | 69 |
| 28 | (bicyclic triazine-dione with 4-(4-chlorobenzyloxy)phenyl) | 166~169 | 60.42 / 60.73 | 4.51 / 4.59 | 11.74 / 11.72 | X = Cl 9.91 / 9.68 | 73 |
| 29 | (pyridazine-dione with 4-CH$_3$-phenyl) | 186~187 | 64.84 / 65.00 | 6.61 / 6.51 | 16.21 / 16.20 | | 68 |
| 30 | (pyridazine-dione with 4-Cl-phenyl) | 118~119.5 | 55.82 / 55.85 | 5.05 / 5.06 | 15.02 / 15.11 | X = Cl 12.68 / 12.61 | 74 |
| 31 | (pyridazine-dione with 4-Br-phenyl) | 134–135 | 48.16 / 48.11 | 4.35 / 4.39 | 12.96 / 12.91 | X = Br 24.55 / 24.41 | 70 |
| 32 | (pyridazine-dione with 3,4-diCl-phenyl) | 133~134 | 49.70 / 49.68 | 4.17 / 4.15 | 13.38 / 13.39 | X = Cl 22.57 / 22.62 | 75 |
| 33 | (pyridazine-dione with 3,5-diCl-phenyl) | 124~125 | 49.70 / 49.66 | 4.17 / 4.21 | 13.38 / 13.37 | X = Cl 22.57 / 22.60 | 74 |
| 34 | (piperidine-dione with 4-OCH$_3$-phenyl) | 134~135 | 61.08 / 61.19 | 6.22 / 6.25 | 15.26 / 15.25 | | 70 |

TABLE 5-continued

| Compd. No. | Structure | Melting point (°C.) | Elementary analysis (%) C | H | N | X | Yield (%) |
|---|---|---|---|---|---|---|---|
| 35 | (structure with 6-membered N-N ring fused to diketopiperazine, N-phenyl-4-NO₂) | 168~169 | 53.79 53.81 | 4.86 4.91 | 19.30 19.41 | | 72 |
| 36 | (structure, N-phenyl-3-CF₃) | 103~104 | 53.67 53.60 | 4.50 4.51 | 13.41 13.48 | | 66 |
| 37 | (structure, N-phenyl-4-OCH₂-C₆H₄-Cl) | 168~170 | 62.26 62.33 | 5.22 5.31 | 10.89 10.84 | X = Cl 9.19 9.12 | 71 |
| 38 | (7-membered ring structure, N-phenyl-4-Cl) | 84~85 | 57.42 57.21 | 5.49 5.50 | 14.31 14.39 | X = Cl 12.07 12.06 | 58 |
| 39 | (7-membered ring structure, N-phenyl-3,5-Cl₂) | 117~119 | 51.23 51.09 | 4.60 4.55 | 12.80 12.68 | X = Cl 21.60 21.41 | |
| 40 | (CH₂)₈ bridged structure, N-phenyl-3,5-Cl₂ | 171~173 | 53.94 53.67 | 5.38 5.31 | 11.80 11.49 | X = Cl 19.91 19.80 | |
| 41 | CH₃ substituted pyrazolidine, N-phenyl-4-Cl | 135~137 | 54.24 54.52 | 4.55 4.61 | 15.82 15.78 | X = Cl 13.35 13.33 | 54 |
| 42 | CH₃ substituted, N-phenyl-3,5-Cl₂ | 152~154 | 48.02 47.99 | 3.69 3.53 | 14.00 14.11 | X = Cl 23.63 23.48 | |
| 43 | CH₃ substituted 6-membered, N-phenyl-4-Cl | 137~139 | 55.82 55.64 | 5.05 4.90 | 15.02 15.19 | X = Cl 12.68 12.80 | 55 |
| 44 | CH₃ substituted 6-membered, N-phenyl-3,5-Cl₂ | 149~150 | 49.70 49.56 | 4.17 4.13 | 13.38 13.27 | 22.57 22.41 | |

TABLE 5-continued

| Compd. No. | Structure | Melting point (°C.) | Elementary analysis (%) C | H | N | X | Yield (%) |
|---|---|---|---|---|---|---|---|
| 45 | CH₃-substituted tetrahydropyridazine-dione with 4-chlorophenyl | 160~162 | 55.82 / 55.88 | 5.05 / 5.21 | 15.02 / 15.11 | X = Cl 12.68 / 12.43 | 66 |
| 46 | CH₃-substituted tetrahydropyridazine-dione with 2,5-dichlorophenyl | 167 | 49.70 / 49.63 | 4.17 / 4.08 | 13.38 / 13.25 | X = Cl 22.57 / 22.42 | |
| 47 | dimethyl-substituted with 4-chlorophenyl | 165~167.5 | 57.24 / 57.25 | 5.49 / 5.50 | 14.31 / 14.22 | X = Cl 12.07 / 12.03 | 47 |
| 48 | dimethyl-substituted with 2,5-dichlorophenyl | 246~248 | 51.23 / 51.58 | 4.60 / 4.28 | 12.80 / 12.64 | X = Cl 21.60 / 21.60 | |
| 49 | dimethyl-substituted with 4-chlorophenyl | 174.5~175.5 | 57.24 / 57.30 | 5.49 / 5.44 | 14.31 / 14.28 | X = Cl 12.07 / 12.00 | |
| 50 | dimethyl-substituted with 2,5-dichlorophenyl | 180~182 | 51.23 / 51.43 | 4.60 / 4.44 | 12.80 / 12.68 | X = Cl 21.60 / 21.23 | |
| 51 | with 3-bromophenyl | 126~127.5 | 46.47 / 46.40 | 3.90 / 3.99 | 13.55 / 13.54 | X = Br 25.77 / 25.72 | 85 |
| 52 | with 3,4-dimethylphenyl | 161.5~163 | 64.84 / 64.88 | 6.61 / 6.69 | 16.21 / 16.21 | | 87 |
| 53 | with 3-methyl-4-chlorophenyl | 151~152 | 55.82 / 55.83 | 5.04 / 5.03 | 15.02 / 15.05 | X = Cl 12.68 / 12.82 | 90 |

TABLE 5-continued

| Compd. No. | Structure | Melting point (°C.) | Elementary analysis (%) | | | | Yield (%) |
|---|---|---|---|---|---|---|---|
| | | | C | H | N | X | |
| 54 | (structure: bicyclic with N-N, two C=O, N-aryl with 3-CH₃, 4-Br) | 174.5~177 | 48.16 48.30 | 4.35 4.15 | 12.96 12.88 | X = Br 24.65 24.66 | 91 |
| 55 | (structure: bicyclic with N-N, two C=O, N-aryl with 3-Br, 4-CH₃) | 163~165 | 48.16 48.19 | 4.35 4.31 | 12.96 12.85 | X = Br 24.65 24.55 | 84 |

TABLE 6

| Compd. No. | Structure | Melting point (°C.) | Elementary analysis (%) | | | | | Ex. No. | Yield (%) |
|---|---|---|---|---|---|---|---|---|---|
| | | | C | H | N | S | X | | |
| 56 | (bicyclic C=S, C=O, N-p-tolyl) | 195~198 | 58.27 58.32 | 5.30 5.45 | 16.99 16.86 | 12.97 13.10 | | 24 | 85 |
| 57 | (bicyclic C=S, C=O, N-p-OCH₃-phenyl) | 149.5~152 | 54.73 54.85 | 4.98 5.07 | 15.96 16.08 | 12.18 12.32 | | 25 | 85 |
| 58 | (bicyclic C=S, C=O, N-p-Cl-phenyl) | 134~135 | 49.34 49.28 | 3.77 3.62 | 15.70 13.78 | 11.98 12.10 | (X = Cl) 13.24 13.31 | 26 | 85 |
| 59 | (bicyclic C=S, C=O, N-2,5-dichlorophenyl) | 164~165.5 | 43.72 43.68 | 3.00 2.97 | 13.91 13.86 | 10.61 10.63 | X = Cl 23.47 23.51 | 33 | 41 |
| 60 | (bicyclic C=S, C=O, N—CH₃) | 144.5~145.5 | 45.38 45.30 | 5.99 6.08 | 22.69 22.65 | 17.31 17.49 | | 24 | 75 |
| 61 | (bicyclic C=S, C=O, N—C₂H₅) | 90.5~93 | 48.22 48.09 | 6.58 6.35 | 21.09 21.13 | 16.09 16.24 | | 24 | 75 |
| 62 | (bicyclic C=S, C=O, N—CH₂—CH=CH₂) | 73~74 | 51.16 51.30 | 6.20 6.33 | 19.89 19.93 | 15.18 15.35 | | 24 | 70 |

TABLE 6-continued

| Compd. No. | Structure | Melting point (°C.) | Elementary analysis (%) C | H | N | S | X | Ex. No. | Yield (%) |
|---|---|---|---|---|---|---|---|---|---|
| 63 | (cyclohexyl derivative) | 137.5~138 | 56.88 / 56.68 | 7.50 / 7.38 | 16.59 / 16.65 | 12.66 / 12.60 | | 24 | 80 |
| 64 | (2-CH₃ phenyl) | 113.5~115 | 59.74 / 59.88 | 5.79 / 5.90 | 16.08 / 16.05 | 12.27 / 12.40 | | 24 | 82 |
| 65 | (3-CH₃ phenyl) | 133~133.5 | 59.74 / 59.91 | 5.79 / 5.95 | 16.08 / 16.10 | 12.27 / 12.43 | | 24 | 82 |
| 66 | (4-CH₃ phenyl) | 182~183.5 | 59.74 / 59.78 | 5.79 / 5.88 | 16.08 / 16.13 | 12.27 / 12.45 | | 26 | 90 |
| 67 | (4-C₄H₉-n phenyl) | 128.5~129.5 | 63.33 / 63.50 | 6.98 / 7.12 | 13.85 / 13.84 | 10.57 / 10.66 | | 24 | 84 |
| 68 | (2,6-diethylphenyl) | $N_D^{27}$ 1.5873 (liquid) | 63.33 / 63.48 | 6.98 / 7.08 | 13.85 / 13.97 | 10.57 / 10.40 | | 24 | 80 |
| 69 | (4-OCH₃ phenyl) | 140~141 | 56.29 / 56.35 | 5.45 / 5.59 | 15.15 / 15.30 | 11.56 / 11.72 | | 24 | 92 |
| 70 | (4-OC₂H₅ phenyl) | 181~183.5 | 57.71 / 57.92 | 5.88 / 5.95 | 14.42 / 14.30 | 11.01 / 11.21 | | 24 | 85 |
| 71 | (4-F phenyl) | 152~153 | 54.32 / 54.40 | 4.56 / 4.71 | 15.84 / 15.80 | 12.09 / 12.22 | | 26 | 90 |
| 72 | (3-Cl phenyl) | 141~142 | 51.15 / 51.28 | 4.29 / 4.38 | 14.91 / 14.85 | 11.38 / 11.49 | X=Cl 12.58 / 12.65 | 24 | 81 |

TABLE 6-continued

| Compd. No. | Structure | Melting point (°C.) | Elementary analysis (%) C | H | N | S | X | Ex. No. | Yield (%) |
|---|---|---|---|---|---|---|---|---|---|
| 73 | (structure with 4-Cl phenyl) | 163.5~165 | 51.15 51.35 | 4.29 4.42 | 14.91 14.96 | 11.38 11.15 | X=Cl 12.58 12.36 | 26 | 86 |
| 74 | (structure with 3,4-diCl phenyl) | 212~214.5 | 45.58 45.70 | 3.51 3.69 | 13.29 13.35 | 10.14 10.32 | X=Cl 22.43 22.28 | 24 | 92 |
| 75 | (structure with 3,5-diCl phenyl) | 199~200.5 | 45.58 45.44 | 3.51 3.60 | 13.29 13.21 | 10.14 10.00 | X=Cl 22.43 22.19 | 27 | 82 |
| 76 | (structure with 4-Br phenyl) | 149~152 | 44.18 44.30 | 3.71 3.92 | 12.88 12.80 | 9.83 9.95 | X=Br 24.50 24.69 | 24 | 92 |
| 77 | (structure with 4-I phenyl) | 180~181.5 | 38.62 38.49 | 3.24 3.08 | 11.26 11.28 | 8.59 8.70 | | 24 | 90 |
| 78 | (structure with 3-CF₃ phenyl) | 133~134 | 49.52 49.69 | 3.84 3.95 | 13.33 13.30 | 10.17 10.35 | | 24 | 83 |
| 79 | (structure with 4-NO₂ phenyl) | 168~169.5 | 49.30 49.45 | 4.14 4.35 | 19.17 19.15 | 10.97 19.95 | 24 | | 95 |
| 80 | (structure with 1-naphthyl) | 159~161 | 64.62 64.48 | 5.09 4.88 | 14.13 14.20 | 10.78 10.98 | | 24 | 90 |
| 81 | (structure with 4-(4-chlorobenzyloxy)phenyl) | 158~159.5 | 58.83 58.80 | 4.68 4.78 | 10.83 10.90 | 8.27 8.42 | X=Cl 9.14 9.02 | 24 | 85 |

TABLE 6-continued

| Compd. No. | Structure | Melting point (°C.) | Elementary analysis (%) C | H | N | S | X | Ex. No. | Yield (%) |
|---|---|---|---|---|---|---|---|---|---|
| 82 | 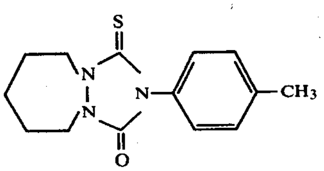 | 208~210 | 61.06 / 61.21 | 6.22 / 6.39 | 15.26 / 15.25 | 11.65 / 11.78 | | 24 | 84 |
| 83 | 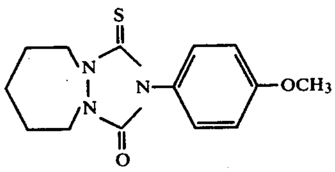 | 185~187 | 57.71 / 58.85 | 5.88 / 5.95 | 14.42 / 14.41 | 11.01 / 11.18 | | 24 | 92 |
| 84 | 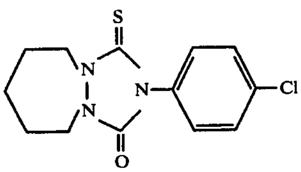 | 154.5~155 | 52.78 / 52.68 | 4.77 / 4.65 | 14.21 / 14.25 | 10.84 / 10.98 | X=Cl 11.99 / 11.80 | 24 | 95 |
| 85 | 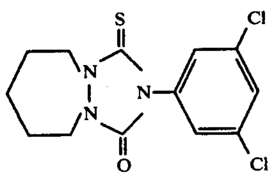 | 168~170 | 47.28 / 47.22 | 3.97 / 3.86 | 12.72 / 12.70 | 9.71 / 9.64 | X=Cl 21.47 / 21.53 | 27 | 77 |
| 86 | 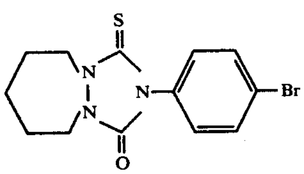 | 150~152 | 43.89 / 43.95 | 4.15 / 4.25 | 12.35 / 12.35 | 9.42 / 9.53 | X=Br 23.49 / 23.30 | 24 | 95 |
| 87 | 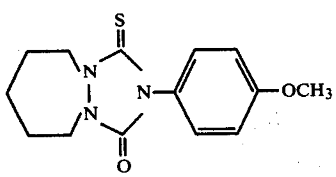 | 156.5~158 | 58.99 / 58.83 | 6.27 / 6.18 | 13.76 / 13.70 | 10.50 / 10.65 | | 24 | 88 |
| 88 | 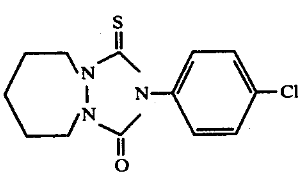 | 124~127 | 54.27 / 54.42 | 5.21 / 5.39 | 13.56 / 13.58 | 10.35 / 10.50 | X=Cl 11.44 / 11.38 | 24 | 90 |
| 89 | 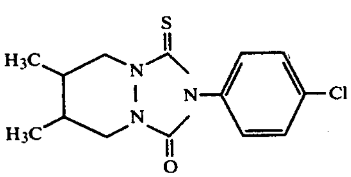 | 239~241 | 54.27 / 54.36 | 5.21 / 5.38 | 13.56 / 13.50 | 10.35 / 10.48 | X=Cl 11.44 / 11.27 | 25 | 95 |
| 90 | 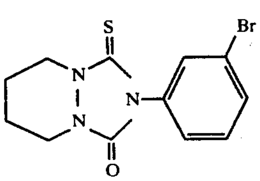 | 168.5~170 | 44.18 / 44.17 | 3.71 / 3.71 | 12.88 / 12.87 | 9.83 / 9.99 | X=Br 24.50 / 24.36 | | 85 |

TABLE 6-continued

| Compd. No. | Structure | Melting point (°C.) | Elementary analysis (%) | | | | | Ex. No. | Yield (%) |
|---|---|---|---|---|---|---|---|---|---|
| | | | C | H | N | S | X | | |
| 91 | (structure: bicyclic N-N ring with C=S and C=O, N-aryl with 3,4-di-CH₃) | 134~136 | 61.06 6.22 15.26 11.64 | | | | | | 71 |
| | | | 61.22 6.39 15.11 11.55 | | | | | | |
| 92 | (structure: bicyclic N-N ring with C=S and C=O, N-aryl with 3-CH₃, 4-Cl) | 169~172 | 52.78 4.77 14.21 10.84 | | | | X=Cl | | 82 |
| | | | 52.69 4.55 14.20 10.99 11.99 | | | | | | |
| | | | | | | | 11.92 | | |
| 93 | (structure: bicyclic N-N ring with C=S and C=O, N-aryl with 4-Br) | 197.5~198.5 | 45.80 4.15 12.35 9.42 | | | | X=Br | | 89 |
| | | | 45.84 4.14 12.35 9.68 23.49 | | | | | | |
| | | | | | | | 23.55 | | |

*Refractive index

TABLE 7

| Compd. No. | Structure | Melting point (°C.) | Elementary analysis (%) | | | | | Ex. No. | Yield (%) |
|---|---|---|---|---|---|---|---|---|---|
| | | | C | H | N | S | X | | |
| 94 | (structure: bicyclic N-N ring with two C=S groups, N-aryl with 4-Cl) | 209~211 | 46.55 3.55 14.81 22.60 | | | | X = Cl | 34 | 75 |
| | | | 46.42 3.40 14.83 22.75 12.49 | | | | | | |
| | | | | | | | 12.55 | | |
| 95 | (structure: bicyclic N-N ring with two C=S groups, N-aryl with 4-CH₃) | 222~224 | 56.28 5.45 15.15 23.12 | | | | | 34 | 81 |
| | | | 56.43 5.59 15.13 23.34 | | | | | | |
| 96 | (structure: bicyclic N-N ring with two C=S groups, N-aryl with 4-OCH₃) | 227~228 | 53.21 5.15 14.32 21.86 | | | | | 34 | 85 |
| | | | 53.38 5.35 14.30 21.95 | | | | | | |
| 97 | (structure: bicyclic N-N ring with two C=S groups, N-aryl with 4-Cl) | 206~208 | 48.39 4.06 14.11 21.53 | | | | X = Cl | 34 | 87 |
| | | | 48.07 4.22 14.16 21.43 11.91 | | | | | | |
| | | | | | | | 11.95 | | |
| 98 | (structure: bicyclic N-N ring with two C=S groups, N-aryl with 2,3-di-Cl) | 282~283 | 43.37 3.34 12.65 19.30 | | | | X = Cl | 34 | 82 |
| | | | 43.28 3.45 12.60 19.44 21.34 | | | | | | |
| | | | | | | | 21.51 | | |

TABLE 7-continued

| Compd. No. | Structure | Melting point (°C.) | Elementary analysis (%) | | | | | Ex. No. | Yield (%) |
|---|---|---|---|---|---|---|---|---|---|
| | | | C | H | N | S | X | | |
| 99 | 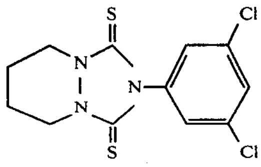 | >250 | 43.38 43.29 | 3.34 3.30 | 12.65 12.58 | 19.30 19.27 | X = Cl 21.34 21.33 | 29 | 65 |
| 100 | 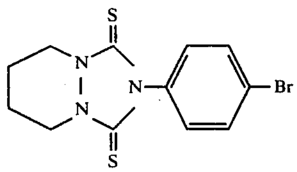 | 230~232 | 42.11 42.28 | 3.53 3.74 | 12.28 12.20 | 18.74 18.98 | X = Br 23.35 23.58 | 34 | 85 |
| 101 | 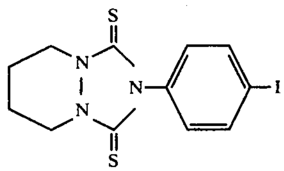 | 254~256 | 37.02 37.28 | 3.11 3.27 | 10.80 10.85 | 16.47 16.59 | | 34 | 75 |
| 102 | 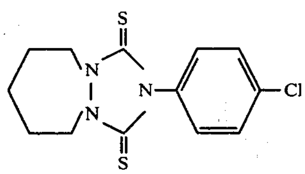 | 200~201 | 50.07 50.18 | 4.53 4.68 | 13.48 13.40 | 20.57 20.39 | X = Cl 11.37 11.50 | 34 | 75 |
| 103 | 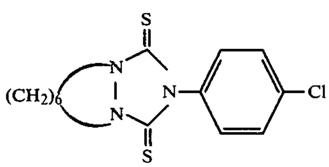 | 217~220 | 51.60 51.82 | 4.95 5.03 | 12.90 12.92 | 19.68 19.80 | X = Cl 10.88 10.97 | 34 | 80 |
| 104 | 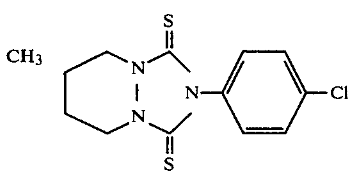 | 213~216 | 50.07 50.21 | 4.53 4.75 | 13.48 13.55 | 20.57 20.37 | X = Cl 11.37 11.46 | 34 | 84 |
| 105 | 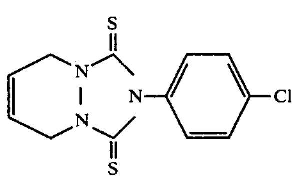 | 207~209 | 48.72 48.59 | 3.41 3.26 | 14.21 14.22 | 21.68 21.80 | X = Cl 11.99 11.78 | 35 | 60 |
| 106 | 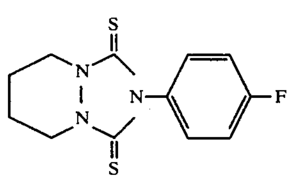 | 238 | 51.22 51.20 | 4.30 4.29 | 14.94 15.02 | 22.79 22.92 | | 33 36 | 73 68 |
| 107 | 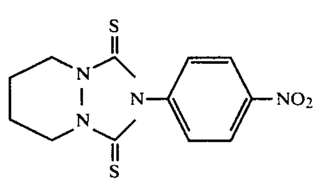 | >300 | 46.73 46.92 | 3.92 3.90 | 18.17 18.05 | 20.80 20.66 | | 33 36 | 68 70 |

TABLE 7-continued

| Compd. No. | Structure | Melting point (°C.) | Elementary analysis (%) C | H | N | S | X | Ex. No. | Yield (%) |
|---|---|---|---|---|---|---|---|---|---|
| 108 | 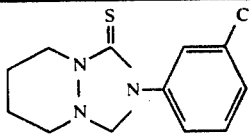 | 219–220 | 48.39 4.06<br>48.55 4.05 | | 14.11<br>14.00 | 21.53<br>21.55 | X = Cl<br>11.91<br>11.77 | 33<br>36 | 78<br>70 |
| 109 | 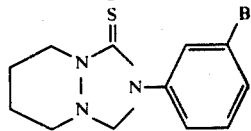 | 246–267 | 42.10 3.53<br>42.11 3.59 | | 12.28<br>12.39 | 18.74<br>18.99 | X = Br<br>23.35<br>23.11 | 33<br>36 | 78<br>69 |
| 110 | 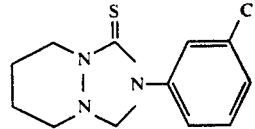 | 202 | 56.29 5.45<br>56.28 5.49 | | 15.15<br>15.33 | 23.12<br>23.35 | | 33<br>36 | 82<br>75 |
| 111 | 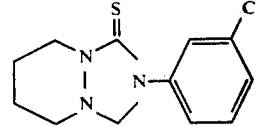 | 230–231 | 47.11 3.65<br>47.01 3.64 | | 12.68<br>12.61 | 19.35<br>19.60 | | 33<br>36 | 75<br>73 |
| 112 | 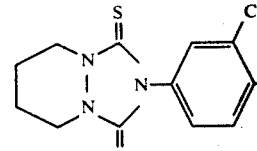 | 159–161 | 57.69 5.88<br>57.87 5.80 | | 14.42<br>14.22 | 22.01<br>22.33 | | 33<br>36 | 76<br>74 |
| 113 | 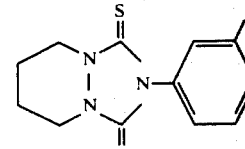 | 239 | 50.06 4.53<br>50.15 4.69 | | 13.48<br>13.39 | 20.56<br>20.80 | X = Cl<br>11.37<br>11.35 | 33<br>36 | 80<br>82 |
| 114 | 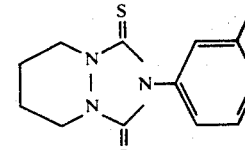 | 267–268 | 43.82 3.96<br>43.89 3.82 | | 11.79<br>11.77 | 18.00<br>18.22 | X = Br<br>22.43<br>22.41 | 33<br>36 | 81<br>78 |
| 115 | 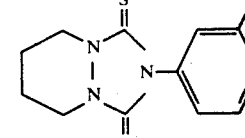 | 271–272 | 43.82 3.96<br>43.80 3.90 | | 11.79<br>11.85 | 18.00<br>18.11 | X = Br<br>22.43<br>22.40 | 33<br>36 | 69<br>75 |

TEST EXAMPLE 1. (PADDY FIELD APPLICATION)

Wagner's pots (1/50 m²) packed with soil from paddy field are employed.

Soil containing seeds of barnyardgrass (*Echinochloa crus-galli*) and toothcup (*Rotala indica*) was spread on the surface area and rice seedlings (the three true leaf stage) were planted. While the depth of water was maintained at 3 cm, after 5 days herbicide according to this invention in the form of granule was uniformly applied to the surface of water in a dosage of 10 g, 20 g, 30 g and 40 g, as active ingredient, per 100 m². Then, the water was drained at a rate of a depth 3 cm/day for 3 days and 25 days after application herbicidal effect and phytotoxicity against rice plant were observed.

For the comparison purpose, similar tests were conducted using a commercially available herbicide comprising N,N-diethyl-S-(4-chlorobenzyl)thiolcarbamate, as a control chemical.

The results are given in Table 8.

The measures of the evaluation of herbicidal effect and phytotoxicity are as follow.

| Figures | Herbicidal Effect | Phytotoxicity |
|---|---|---|
| 0 | None | None |
| 1 | Trace | Trace |
| 2 | Slight | Slight |
| 3 | Moderate | Moderate |
| 4 | Severe | Severe |
| 5 | Dead | Dead |

TABLE 8

| Compd. No. | Dosage g/100m² | Herbicidal effect Barnyard-grass | toothcup | Phyto-toxicity |
|---|---|---|---|---|
| 3 | 40 | 4 | 5 | 0 |
|  | 20 | 2 | 5 | 0 |
|  | 10 | 2 | 5 | 0 |
| 4 | 40 | 4 | 5 | 0 |
|  | 20 | 3 | 5 | 0 |
|  | 10 | 2 | 4 | 0 |
| 6 | 40 | 5 | 5 | 0 |
|  | 20 | 5 | 5 | 0 |
|  | 10 | 5 | 5 | 0 |
| 8 | 40 | 3 | 3 | 0 |
|  | 20 | 2 | 2 | 0 |
|  | 10 | 0 | 0 | 0 |
| 12 | 40 | 4 | 5 | 0 |
|  | 20 | 2 | 5 | 0 |
|  | 10 | 1 | 4 | 0 |
| 16 | 40 | 5 | 5 | 1 |
|  | 20 | 3 | 5 | 0 |
|  | 10 | 2 | 4 | 0 |
| 25 | 40 | 3 | 5 | 0 |
|  | 20 | 2 | 4 | 0 |
|  | 10 | 1 | 4 | 0 |
| 56 | 30 | 4 | 5 | 0 |
|  | 10 | 3 | 4 | 0 |
| 57 | 30 | 5 | 5 | 1 |
|  | 10 | 4 | 5 | 0 |
| 60 | 30 | 4 | 4 | 0 |
|  | 10 | 3 | 4 | 0 |
| 62 | 30 | 4 | 4 | 0 |
|  | 10 | 3 | 4 | 0 |
| 64 | 30 | 5 | 5 | 0 |
|  | 10 | 4 | 4 | 0 |
| 66 | 30 | 5 | 5 | 0 |
|  | 10 | 5 | 5 | 0 |
| 67 | 30 | 5 | 5 | 0 |
|  | 10 | 4 | 5 | 0 |
| 69 | 30 | 5 | 5 | 0 |
|  | 10 | 5 | 5 | 0 |
| 71 | 30 | 5 | 5 | 0 |
|  | 10 | 5 | 5 | 0 |
| 74 | 30 | 5 | 5 | 0 |
|  | 10 | 4 | 5 | 0 |
| 78 | 30 | 5 | 5 | 0 |
|  | 10 | 3 | 4 | 0 |
| 79 | 30 | 5 | 5 | 1 |
|  | 10 | 5 | 5 | 0 |
| 81 | 30 | 5 | 5 | 0 |
|  | 10 | 5 | 5 | 0 |
| 82 | 30 | 5 | 5 | 0 |
|  | 10 | 4 | 5 | 0 |
| 84 | 30 | 5 | 5 | 0 |
|  | 10 | 5 | 5 | 0 |
| 88 | 30 | 5 | 5 | 0 |
|  | 10 | 4 | 5 | 0 |
| 89 | 40 | 5 | 5 | 0 |
|  | 20 | 5 | 5 | 0 |
|  | 10 | 4 | 5 | 0 |
| 94 | 30 | 5 | 5 | 0 |
|  | 10 | 4 | 5 | 0 |
| 95 | 30 | 4 | 5 | 0 |
|  | 10 | 3 | 4 | 0 |
| 97 | 30 | 5 | 5 | 0 |
|  | 10 | 5 | 5 | 0 |
| 98 | 30 | 5 | 5 | 0 |
|  | 10 | 4 | 4 | 0 |
| 102 | 30 | 5 | 5 | 0 |
|  | 10 | 5 | 5 | 0 |
| 103 | 30 | 5 | 5 | 0 |
|  | 10 | 5 | 5 | 0 |
| Control | 30 | 5 | 5 | 0 |
|  | 10 | 5 | 4 | 0 |
| No Application | — | 0 | 0 | 0 |
| 51 | 40 | 5 | 5 | 0 |
|  | 20 | 4 | 5 | 0 |
|  | 10 | 3 | 5 | 0 |
| 53 | 40 | 5 | 5 | 0 |
|  | 20 | 5 | 5 | 0 |
|  | 10 | 5 | 5 | 0 |
| 54 | 40 | 5 | 5 | 0 |
|  | 20 | 5 | 5 | 0 |
|  | 10 | 4 | 5 | 0 |
| 90 | 30 | 5 | 5 | 0 |
|  | 10 | 4 | 5 | 0 |
| 91 | 30 | 5 | 5 | 0 |
|  | 10 | 4 | 5 | 0 |
| 93 | 30 | 5 | 5 | 0 |
|  | 10 | 5 | 5 | 0 |
| 106 | 30 | 5 | 5 | 0 |
|  | 10 | 5 | 5 | 0 |
| 109 | 30 | 5 | 5 | 0 |
|  | 10 | 4 | 5 | 0 |
| 110 | 30 | 4 | 4 | 0 |
|  | 10 | 3 | 3 | 0 |
| 112 | 30 | 3 | 4 | 0 |
|  | 10 | 2 | 3 | 0 |
| 113 | 30 | 5 | 5 | 0 |
|  | 10 | 4 | 5 | 0 |

TEST EXAMPLE 2. (SOIL APPLICATION)

Rice, soybean and corn were seeded at a depth of 2–3 cm in 1/50 m² Wagner's pots containing soil from field, and soil containing seeds of crab-grass (*Digitaria adscendens*) and common purslane (*Partulaca oleracea*) were spread on the surface area, then aqueous dilutions of the wettable powder according to this invention were applied in a dosage per 100 m² of 10 g, 20 g, 30 g and 40 g to the surface area. After 25 days from the application, herbicidal effect and phytotoxity were observed.

For the comparison purpose, the same tests were conducted using a commercially available herbicide comprising 3-(3,4-dichlorophenyl)-1,1-dimethylurea as a control chemical.

The results are given in Table 9.

TABLE 9

| Compd. No. | Dosage g/100m² | Herbicidal effect Crab-grass | Common purslane | Phytotoxicity Rice | Soy-bean | Corn |
|---|---|---|---|---|---|---|
| 2 | 40 | 4 | 4 | 0 | 0 | 0 |
|  | 20 | 2 | 3 | 0 | 0 | 0 |
| 3 | 40 | 5 | 5 | 0 | 0 | 0 |
|  | 20 | 4 | 5 | 0 | 0 | 0 |
| 5 | 40 | 3 | 5 | 0 | 0 | 0 |
|  | 20 | 1 | 3 | 0 | 0 | 0 |
| 6 | 40 | 5 | 5 | 0 | 0 | 0 |
|  | 20 | 5 | 5 | 0 | 0 | 0 |
| 9 | 40 | 5 | 5 | 1 | 0 | 1 |
|  | 20 | 5 | 5 | 0 | 0 | 0 |
| 10 | 40 | 5 | 5 | 0 | 0 | 0 |
|  | 20 | 5 | 5 | 0 | 0 | 0 |
| 13 | 40 | 5 | 5 | 0 | 0 | 0 |
|  | 20 | 4 | 5 | 0 | 0 | 0 |
| 15 | 40 | 4 | 4 | 0 | 0 | 0 |
|  | 20 | 2 | 3 | 0 | 0 | 0 |
| 17 | 40 | 4 | 5 | 0 | 0 | 0 |

TABLE 9-continued

| Compd. No. | Dosage g/100m² | Herbicidal effect Crab-grass | Common purslane | Phytotoxicity Rice | Soy-bean | Corn |
|---|---|---|---|---|---|---|
| 19 | 20 | 3 | 4 | 0 | 0 | 0 |
|    | 40 | 3 | 4 | 0 | 0 | 0 |
| 20 | 20 | 1 | 2 | 0 | 0 | 0 |
|    | 40 | 4 | 5 | 0 | 0 | 0 |
| 22 | 20 | 3 | 4 | 0 | 0 | 0 |
|    | 40 | 5 | 5 | 1 | 0 | 1 |
| 23 | 20 | 4 | 4 | 0 | 0 | 0 |
|    | 40 | 4 | 4 | 0 | 0 | 0 |
| 26 | 20 | 2 | 3 | 0 | 0 | 0 |
|    | 40 | 4 | 4 | 0 | 0 | 0 |
| 29 | 20 | 2 | 3 | 0 | 0 | 0 |
|    | 40 | 4 | 5 | 0 | 0 | 0 |
| 30 | 20 | 3 | 4 | 0 | 0 | 0 |
|    | 40 | 5 | 5 | 1 | 0 | 1 |
| 31 | 20 | 4 | 4 | 0 | 0 | 0 |
|    | 40 | 5 | 5 | 0 | 0 | 0 |
| 32 | 20 | 4 | 4 | 0 | 0 | 0 |
|    | 40 | 5 | 5 | 0 | 0 | 0 |
| 34 | 20 | 4 | 4 | 0 | 0 | 0 |
|    | 40 | 4 | 5 | 0 | 0 | 0 |
| 35 | 20 | 2 | 3 | 0 | 0 | 0 |
|    | 40 | 4 | 5 | 0 | 0 | 0 |
| 49 | 20 | 3 | 3 | 0 | 0 | 0 |
|    | 30 | 5 | 5 | 0 | 0 | 0 |
|    | 10 | 4 | 5 | 0 | 0 | 0 |
| 58 | 30 | 5 | 5 | 2 | 0 | 1 |
|    | 10 | 4 | 5 | 0 | 0 | 0 |
| 61 | 30 | 4 | 5 | 0 | 0 | 0 |
|    | 10 | 3 | 5 | 0 | 0 | 0 |
| 63 | 30 | 4 | 5 | 0 | 0 | 0 |
|    | 10 | 3 | 3 | 0 | 0 | 0 |
| 65 | 30 | 4 | 5 | 0 | 0 | 0 |
|    | 10 | 3 | 4 | 0 | 0 | 0 |
| 66 | 30 | 5 | 5 | 1 | 0 | 0 |
|    | 10 | 4 | 5 | 0 | 0 | 0 |
| 68 | 30 | 5 | 5 | 0 | 0 | 0 |
|    | 10 | 3 | 4 | 0 | 0 | 0 |
| 70 | 30 | 5 | 5 | 0 | 0 | 0 |
|    | 10 | 4 | 5 | 0 | 0 | 0 |
| 72 | 30 | 5 | 5 | 0 | 0 | 0 |
|    | 10 | 4 | 5 | 0 | 0 | 0 |
| 73 | 30 | 5 | 5 | 1 | 0 | 0 |
|    | 10 | 5 | 5 | 0 | 0 | 0 |
| 76 | 30 | 5 | 5 | 0 | 0 | 0 |
|    | 10 | 5 | 5 | 0 | 0 | 0 |
| 77 | 30 | 5 | 5 | 0 | 0 | 0 |
|    | 10 | 5 | 5 | 0 | 0 | 0 |
| 80 | 30 | 4 | 5 | 0 | 0 | 0 |
|    | 10 | 3 | 3 | 0 | 0 | 0 |
| 83 | 30 | 5 | 5 | 0 | 0 | 0 |
|    | 10 | 5 | 5 | 0 | 0 | 0 |
| 86 | 30 | 5 | 5 | 0 | 0 | 0 |
|    | 10 | 5 | 5 | 0 | 0 | 0 |
| 87 | 30 | 5 | 5 | 0 | 0 | 0 |
|    | 10 | 4 | 4 | 0 | 0 | 0 |
| 96 | 30 | 5 | 5 | 1 | 0 | 0 |
|    | 10 | 5 | 5 | 0 | 0 | 0 |
| 100 | 30 | 5 | 5 | 0 | 0 | 0 |
|     | 10 | 5 | 5 | 0 | 0 | 0 |
| 101 | 30 | 5 | 5 | 0 | 0 | 0 |
|     | 10 | 4 | 4 | 0 | 0 | 0 |
| 104 | 30 | 5 | 5 | 0 | 0 | 0 |
|     | 10 | 5 | 5 | 0 | 0 | 0 |
| 105 | 30 | 5 | 5 | 0 | 0 | 0 |
|     | 10 | 5 | 5 | 0 | 0 | 0 |
|     | 30 | 5 | 5 | 1 | 0 | 0 |
| Control | 10 | 4 | 5 | 0 | 0 | 0 |
| No Application | — | 0 | 0 | 0 | 0 | 0 |
| 52 | 40 | 4 | 5 | 0 | 0 | 0 |
|    | 20 | 3 | 4 | 0 | 0 | 0 |
| 55 | 40 | 3 | 4 | 0 | 0 | 0 |
|    | 20 | 2 | 2 | 0 | 0 | 0 |
| 90 | 30 | 5 | 5 | 0 | 0 | 0 |
|    | 10 | 4 | 5 | 0 | 0 | 0 |
| 92 | 30 | 5 | 5 | 0 | 0 | 0 |
|    | 10 | 5 | 5 | 0 | 0 | 0 |
| 93 | 30 | 5 | 5 | 0 | 0 | 0 |
|    | 10 | 5 | 5 | 0 | 0 | 0 |
| 107 | 30 | 5 | 5 | 0 | 0 | 0 |
|     | 10 | 4 | 4 | 0 | 0 | 0 |
| 108 | 30 | 4 | 4 | 0 | 0 | 0 |
|     | 10 | 3 | 3 | 0 | 0 | 0 |
| 110 | 30 | 4 | 4 | 0 | 0 | 0 |
|     | 10 | 2 | 3 | 0 | 0 | 0 |
| 114 | 30 | 5 | 5 | 0 | 0 | 0 |
|     | 10 | 4 | 5 | 0 | 0 | 0 |
| 115 | 30 | 4 | 4 | 0 | 0 | 0 |
|     | 10 | 3 | 3 | 0 | 0 | 0 |

TEST EXAMPLE 3.(FOLIAR APPLICATION)

Barnyardgrass (*Echinochloa crus-galli*), crab-grass (*Digitaria adscendes*) and radish (*Raphanus sativas*) were seeded in 1/50 m² Wagner's pots and after growing the plants emulsions containing 0.1%, 0.25%, 0.3% and 0.50% of active ingredient according to this invention were sprayed on the foliage in an amount of 10 l per 100 m² by a small pressurized spray-gun (0.5–1.0 kg/cm²).

After 20 days from the application, herbicidal effects wre observed.

The times at which the herbicide was sprayed were 2–3 leaf stage in cases of barnyardgrass and crab-grass and first true leaf stage in case of radish.

For comparison, the same tests were conducted by a commercially available herbicide comprising 3,4-dichloropropione anilide as a control chemical.

The results are given in Table 10.

TABLE 10

| Compd. No. | Concent. (%) | Herbicidal effect Barnyard-grass | Crab-grass | Radish |
|---|---|---|---|---|
| 1 | 0.50 | 3 | 4 | 4 |
|   | 0.25 | 2 | 3 | 3 |
| 7 | 0.50 | 4 | 5 | 5 |
|   | 0.25 | 3 | 5 | 4 |
| 9 | 0.50 | 5 | 5 | 5 |
|   | 0.25 | 3 | 5 | 5 |
| 11 | 0.50 | 4 | 5 | 5 |
|    | 0.25 | 3 | 4 | 4 |
| 21 | 0.50 | 5 | 5 | 5 |
|    | 0.25 | 4 | 5 | 5 |
| 30 | 0.50 | 5 | 5 | 5 |
|    | 0.25 | 4 | 5 | 5 |
| 38 | 0.50 | 3 | 4 | 4 |
|    | 0.25 | 2 | 3 | 3 |
| 49 | 0.3 | 4 | 5 | 5 |
|    | 0.1 | 3 | 3 | 4 |
| 57 | 0.3 | 4 | 5 | 5 |
|    | 0.1 | 3 | 4 | 5 |
| 58 | 0.3 | 5 | 5 | 5 |
|    | 0.1 | 3 | 5 | 5 |
| 69 | 0.3 | 5 | 5 | 5 |
|    | 0.1 | 4 | 5 | 5 |
| 71 | 0.3 | 5 | 5 | 5 |
|    | 0.1 | 5 | 5 | 5 |
| 73 | 0.3 | 5 | 5 | 5 |
|    | 0.1 | 5 | 5 | 5 |
| 76 | 0.3 | 5 | 5 | 5 |
|    | 0.1 | 5 | 5 | 5 |
| 77 | 0.3 | 4 | 5 | 5 |
|    | 0.1 | 3 | 4 | 4 |
| 83 | 0.3 | 4 | 5 | 5 |
|    | 0.1 | 3 | 4 | 4 |
| 84 | 0.3 | 5 | 5 | 5 |
|    | 0.1 | 5 | 5 | 5 |
| 88 | 0.3 | 4 | 5 | 5 |

TABLE 10-continued

| Compd. No. | Concent. (%) | Herbicidal effect | | |
|---|---|---|---|---|
| | | Barnyard-grass | Crab-grass | Radish |
| | 0.1 | 3 | 5 | 4 |
| 89 | 0.3 | 5 | 5 | 5 |
| | 0.1 | 4 | 4 | 5 |
| 94 | 0.3 | 5 | 5 | 5 |
| | 0.1 | 5 | 5 | 5 |
| 97 | 0.3 | 5 | 5 | 5 |
| | 0.1 | 5 | 5 | 5 |
| 102 | 0.3 | 5 | 5 | 5 |
| | 0.1 | 4 | 5 | 5 |
| 105 | 0.3 | 5 | 5 | 5 |
| | 0.1 | 4 | 5 | 5 |
| | 0.3 | 5 | 5 | 5 |
| Control | 0.1 | 4 | 5 | 4 |
| No Application | — | 0 | 0 | 0 |
| 51 | 0.50 | 4 | 5 | 5 |
| | 0.25 | 2 | 4 | 5 |
| 52 | 0.50 | 3 | 4 | 4 |
| | 0.25 | 2 | 3 | 3 |
| 55 | 0.50 | 3 | 3 | 4 |
| | 0.25 | 2 | 2 | 3 |
| 91 | 0.3 | 3 | 4 | 4 |
| | 0.1 | 2 | 3 | 3 |
| 92 | 0.3 | 5 | 5 | 5 |
| | 0.1 | 4 | 5 | 5 |
| 93 | 0.3 | 5 | 5 | 5 |
| | 0.1 | 4 | 5 | 5 |
| 106 | 0.3 | 5 | 5 | 5 |
| | 0.1 | 4 | 5 | 5 |
| 108 | 0.3 | 4 | 5 | 5 |
| | 0.1 | 3 | 4 | 4 |
| 111 | 0.3 | 3 | 3 | 4 |
| | 0.1 | 2 | 3 | 3 |
| 112 | 0.3 | 3 | 4 | 4 |
| | 0.1 | 2 | 3 | 3 |
| 114 | 0.3 | 5 | 5 | 5 |
| | 0.1 | 4 | 5 | 5 |

What is claimed is:

1. 1,2-Alkylene-4-substituted urazole derivatives represented by the formula

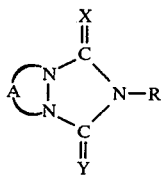

wherein A represents alkylene or alkenylene containing 3–6 carbon atoms, and wherein the adjacent nitrogen atoms of the urazole radical are bonded to different carbons of the A group, X and Y represent oxygen of sulfur respectively, but when A is alkenylene both X and Y are sulfur, R represents phenyl substituted in the 3- or 4- position with one or two substituents selected from halogen, lower alkyl, lower alkoxy, nitro halogenated benzyloxy or trihalomethyl.

2. 1,2-Alkylene-4-substituted urazole compounds represented by formula

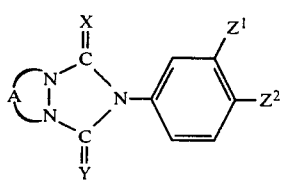

wherein A represents alkylene or alkenylene containing 3–6 carbon atoms, and wherein the adjacent nitrogen atoms of the urazole radical are bonded to different carbons of the A group, X and Y represent oxygen or sulfur, respectively, but when A is alkenylene both X and Y are sulfur, $Z^1$ represents hydrogen, halogen, lower alkyl or trihalomethyl, and $Z^2$ represents hydrogen, halogen, lower alkyl, lower alkoxy, nitro or halogenated benzyloxy; provided that $Z^1$ and $Z^2$ are not both hydrogen.

3. A compound of the formula

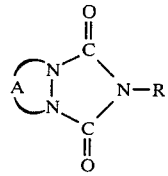

wherein A represents alkylene having 2–8 carbon atoms which may have at least one methyl group and wherein the adjacent nitrogen atoms of urazole radical are bonded to different carbons of the A group, and R represents phenyl having at least one substituent selected from halogen, lower alkyl having 1–4 carbon atoms, lower alkoxy having 1–4 carbon atoms, nitro, monochlorobenzyloxy, or trifluoromethyl; or naphthyl; or a compound of the formula

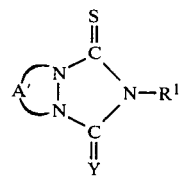

wherein A' represents alkylene having 2–8 carbon atoms, or butenylene which may have at least one methyl group as a side chain and wherein the adjacent nitrogen atoms of the urazole radical are bonded to different carbons of the A' group, Y represents oxygen or sulfur, but when A' is butenylene Y is sulfur, and R' represents phenyl which is substituted with up to three halogens, lower alkyl having 1–4 carbon atoms, lower alkoxy having 1–4 carbon atoms, nitro, halogenated benzyloxy or trihalomethyl; or napthyl.

4. A herbicidal composition consisting essentially of an effective amount of a compound of claims 1, 2 or 3 in combination with an inert agricultural adjuvant.

5. 1,2-Alkylene-4-substituted urazole compounds according to claim 2, wherein $Z^1$ represents hydrogen, methyl or halogen and $Z^2$ represents halogen or halogenated benzyloxy.

6. 1,2-Alkylene-4-substituted urazole compounds according to claim 2, wherein $Z^1$ represents hydrogen, methyl or halogen, $Z^2$ represents halogen or halogenated benzyloxy, X represents sulfur and Y represents oxygen or sulfur.

7. 1,2-Alkylene-4-substituted urazole compounds according to claim 2, wherein $Z^1$ represents hydrogen, methyl or halogen, $Z^2$ represents halogen or halogenated benzyloxy, X and Y represent oxygen.

8. 1,2-Alkylene-4-substituted urazole compounds according to claim 1, wherein A represents alkylene or alkenylene containing 3–5 carbon atoms, $Z^2$ represents halogen or halogenated benzyloxy and $Z^1$ represents hydrogen, methyl or halogen.

9. 1,2-Alkylene-4-substituted urazole compounds according to claim 2, wherein A represents tetramethylene or 2-butenylene, $Z^1$ represents hydrogen, methyl or halogen and $Z^2$ represent halogen or halogenated benzyloxy.

10. 1,2-Alkylene-4-substituted compounds according to claim 1 or 2, wherein A represents tetramethylene or 2-butenylene group.

11. 1,2-Alkylene-4-substituted compounds according to claims 1 or 2, wherein both X and Y represent oxygen.

12. 1,2-Alkylene-4-substituted compounds according to claim 1 or 2, wherein X represents sulfur and Y represents oxygen or sulfur.

13. 1,2-Tetramethylene-4-(4'-chlorophenyl)urazole.

14. 1,2-Tetramethylene-4-(4'-bromophenyl)urazole.

15. 1,2-Tetramethylene-4-(4'-iodophenyl)urazole.

16. 1,2-Tetramethylene-4-(4'-fluorophenyl)urazole.

17. 1,2-Tetramethylene-4-(4'-(4''-chlorobenzyloxy)phenyl) urazole.

18. 1,2-Tetramethylene-4-(4'-chlorophenyl)monothiourazole.

19. 1,2-Tetramethylene-4-(4'-bromophenyl)monothiourazole.

20. 1,2-Tetramethylene-4-(4'-iodophenyl)monothiourazole.

21. 1,2-Tetramethylene-4-(4'-fluorophenyl)monothiourazole.

22. 1,2-Tetramethylene-4-(4'-(4''-chlorobenzyloxy)phenyl)-monothiourazole.

23. 1,2-Tetramethylene-4(4'-chlorophenyl)dithiourazole.

24. 1,2-Tetramethylene-4(4'-bromophenyl)dithiourazole.

25. 1,2-Tetramethylene-4(4'-iodophenyl)dithiourazole.

26. 1,2-Tetramethylene-4(4'-fluorophenyl)dithiourazole.

27. 1,2-Tetramethylene-4-(4'-(4''-chlorobenzyloxy)phenyl)dithiourazole.

28. 1,2-Trimethylene-4-(3,5-dichlorophenyl)urazole.

29. 1,2-Tetramethylene-4-(3,5-dichlorophenyl) urazole.

* * * * *